United States Patent
Pasquier et al.

(10) Patent No.: US 7,537,620 B2
(45) Date of Patent: May 26, 2009

(54) AGENT FOR COLORING KERATIN FIBERS

(75) Inventors: Cecile Pasquier, Marly (CH); Caroline Kiener, Marly (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 67 days.

(21) Appl. No.: 10/589,369

(22) PCT Filed: Nov. 16, 2004

(86) PCT No.: PCT/EP2004/012983

§ 371 (c)(1),
(2), (4) Date: Mar. 22, 2007

(87) PCT Pub. No.: WO2005/079733

PCT Pub. Date: Sep. 1, 2005

(65) Prior Publication Data

US 2007/0258928 A1    Nov. 8, 2007

(30) Foreign Application Priority Data

Feb. 21, 2004  (DE)  ........................ 10 2004 008 603

(51) Int. Cl.
*A61Q 5/10* (2006.01)
*C09B 44/08* (2006.01)

(52) U.S. Cl. .................. 8/405; 8/406; 8/437; 8/455; 8/466; 8/570; 8/571; 8/575; 132/202; 132/208; 534/604

(58) Field of Classification Search ............ 8/405, 8/406, 437, 455, 466, 570, 571, 575; 534/604; 132/202, 208
See application file for complete search history.

(56) References Cited

U.S. PATENT DOCUMENTS 4,046,752 A * 9/1977 Hohmann et al. ........... 534/607
4,269,768 A * 5/1981 Neeb et al. .................. 534/589

FOREIGN PATENT DOCUMENTS

DE    28 22 912     11/1979
DE    36 02 587     7/1987
DE    101 18 271    3/2002

OTHER PUBLICATIONS

STIC Search Report dated Jul. 18, 2008.*

* cited by examiner

*Primary Examiner*—Eisa B Elhilo
(74) *Attorney, Agent, or Firm*—Michael J. Striker

(57) ABSTRACT

The present invention has for an object agents for dyeing keratin fibers, characterized in that they contain at least one thiazoliumazo dye of general formula (I).

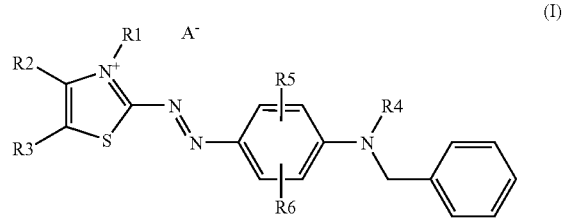

40 Claims, No Drawings

AGENT FOR COLORING KERATIN FIBERS

CROSS-REFERENCE TO RELATED APPLICATIONS

This application is a PCT/EP04/12983 filed on Nov. 16, 2004 and claims priority of the German application No. 10 2004 008 603.6 filed on Feb. 21, 2004.

FIELD OF THE INVENTION

The present invention has for an object agents for coloring keratin fibers, for example wool, furs and particularly human hair, and which contain thiazoliumazo dyes.

BACKGROUND OF THE INVENTION

Two coloring methods are usually used for the color-changing treatment of keratin fibers. By the first method, the coloring is accomplished with oxidative or permanent colorants by use of a mixture of different developers and couplers and an oxidant. By this method, if necessary, it is possible to add a direct (non-oxidative) dye if the coloring result is to be adjusted or special coloring effects are to be achieved. The second method involves the exclusive use of direct dyes which in an appropriate carrier composition are applied to the fibers. This method is easy to apply, very gentle and causes only minor damage to the keratin fibers. The direct dyes used for this purpose are subject to many requirements. For example, they must be unobjectionable in toxicological and dermatological terms and must make it possible to attain colorations of a desired intensity which, among other things, presupposes sufficient water solubility. Moreover, the colorations obtained are required to exhibit good light stability, acid resistance and abrasion resistance.

The advantages of direct coloring over oxidative coloring lie in generally lower hair damage, because normally the former method involves working at low pH values (below 9) and without an oxidant. Direct dyes are also used in various ways as color shade-adjusting aids in oxidative colorants. For a direct (non-oxidative) colorant for keratin fibers it is usually necessary to use a combination of different non-oxidative dyes. Because the selection of dyes that can be used in colorants for keratin fibers is limited, a need for such dyes continues to exist.

SUMMARY OF THE INVENTION

We have now found that certain thiazoliumazo dyes color keratin fibers in an intense blue to violet color and that they exhibit unusually good perspiration resistance.

DETAILED DESCRIPTION OF THE INVENTION

Hence, the present invention has for an object an agent for coloring keratin fibers, particularly human hair, said agent being characterized in that it contains at least one thiazoliumazo dye of general formula (I)

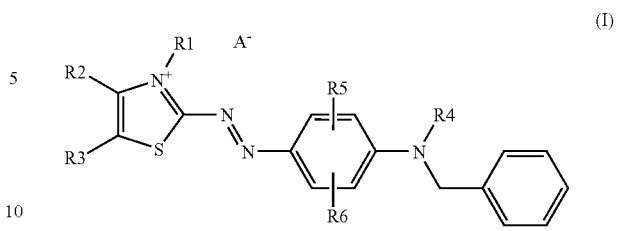

wherein

R1 stands for a saturated or unsaturated ($C_1$-$C_{12}$)-alkyl group, a ($C_1$-$C_{12}$)-alkyl group substituted with a halogen atom (F, Cl, Br, I), a hydroxy-($C_1$-$C_{12}$)-alkyl group, a ($C_1$-$C_6$)-alkoxy-($C_1$-$C_{12}$)-alkyl group, an amino-($C_1$-$C_{12}$)-alkyl group, a ($C_1$-$C_6$)-alkylamino-($C_1$-$C_{12}$)-alkyl group, a di($C_1$-$C_6$)-alkylamino-($C_1$-$C_{12}$)-alkyl group, a cyano-($C_1$-$C_{12}$)-alkyl group, a substituted or unsubstituted phenyl group or a substituted or unsubstituted benzyl group;

R2 and R3 can be equal or different and independently of each other stand for hydrogen, a halogen atom (F, Cl, Br, I), a saturated or unsaturated ($C_1$-$C_{12}$)-alkyl group, ($C_1$-$C_{12}$)-alkoxy group, a nitro group, an amino group, a ($C_1$-$C_{12}$)-alkylamino group, a di($C_1$-$C_{12}$)-alkylamino group, a ($C_1$-$C_{12}$)-hydroxyalkylamino group, a di($C_1$-$C_{12}$)-hydroxyalkylamino group, a substituted or unsubstituted phenyl group or a substituted or unsubstituted heteroaryl group;

R4 stands for hydrogen, a saturated or unsaturated ($C_1$-$C_{12}$)-alkyl group, a halogen (F, Cl, Br, I)-substituted ($C_1$-$C_{12}$)-alkyl group, a hydroxy-($C_1$-$C_{12}$)-alkyl group, an amino-($C_1$-$C_{12}$)-alkyl group or a benzyl group;

R5 and R6 can be equal or different and independently of each other stand for hydrogen, a halogen atom (F, Cl, Br, I), a saturated or unsaturated ($C_1$-$C_{12}$)-alkyl group, a hydroxyl group, a ($C_1$-$C_{12}$)-alkoxy group, a cyano group, a nitro group, an amino group, a ($C_1$-$C_{12}$)-alkylamino group or a di($C_1$-$C_{12}$)-alkylamino group, and $A^-$ stands for an anion of an organic or inorganic acid.

Preferred among the afore-said compounds of formula (I) are those wherein R1 stands for a saturated or unsaturated ($C_1$-$C_{12}$)-alkyl group, the compounds wherein R1 stands for a saturated or unsaturated ($C_1$-$C_{12}$)-alkyl group and R4 stands for a saturated or unsaturated ($C_1$-$C_{12}$)-alkyl group being particularly preferred;

$A^-$ preferably stands for a chloride, bromide, iodide, hydrogen sulfate, sulfate, toluenesulfonate, monomethylsulfate, hexafluorophosphate, hexafluoroantimonate, tetrafluoroborate, tetraphenylborate, formate, acetate or propionate among which the chloride ion, bromide ion, monomethylsulfate ion and acetate ion are particularly preferred.

Suitable compounds of general formula (I) are, for example, the following: 3-methyl-2-{[[4-[methyl(phenylmethyl)amino]phenyl]azo}thiazolium chloride, 3-methyl-2-{[4-[methyl(phenylmethyl)amino]phenyl]azo}thiazolium bromide, 3-methyl-2-{[4-[methyl(phenylmethyl)amino]phenyl]azo}thiazolium monomethylsulfate, 3-methyl-2-{[4-[methyl(phenylmethyl)amino]phenyl]azo}thiazolium acetate, 3,4-dimethyl-2-{[4-[methyl(phenylmethyl)aminophenyl]azo}thiazolium chloride, 3,4-dimethyl-2-{[4-[methyl(phenylmethyl)aminophenyl]azo}thiazolium bromide, 3,4-dimethyl-2-{[4-[methyl(phenylmethyl)aminophenyl]azo}thiazolium monomethylsulfate, 3,4-dimethyl-2-{[4-

[methyl(phenylmethyl)aminophenyl]azo}thiazolium acetate, 3,5-dimethyl-2-{[4-[methyl(phenylmethyl)aminophenyl]azo}thiazolium chloride, 3,5-dimethyl-2-{[4-[methyl(phenylmethyl)aminophenyl]azo}thiazolium bromide, 3,5-dimethyl-2-{[4-[methyl(phenylmethyl)aminophenyl]azo}thiazolium monomethylsulfate, 3,5-dimethyl-2-{[4-[methyl(phenylmethyl)aminophenyl]azo}thiazolium acetate, 3,4,5-trimethyl-2-{[4-[methyl(phenylmethyl)aminophenyl]azo}thiazolium chloride, 3,4,5-trimethyl-2-{[4-[methyl(phenylmethyl)aminophenyl]azo}thiazolium bromide, 3,4,5-trimethyl-2-{[4-[methyl(phenylmethyl)amino]phenyl]azo]thiazolium monomethylsulfate, 3,4,5-trimethyl-2-{[4-[methyl(phenylmethyl)aminophenyl]azo}thiazolium acetate, 5-bromo-3-methyl-2-[[4-[methyl(phenylmethyl)amino]phenyl]azo]thiazolium chloride, 5-bromo-3-methyl-2-[[4-[methyl(phenylmethyl)amino]phenyl]azo]thiazolium bromide, 5-bromo-3-methyl-2-[[4-[methyl(phenylmethyl)amino]phenyl]azo]thiazolium monomethylsulfate, 5-bromo-3-methyl-2-[[4-[methyl(phenylmethyl)amino]phenyl]azo]thiazolium acetate, 5-methoxy-3-methyl-2-[[4-[methyl(phenylmethyl)amino]phenyl]azo]thiazolium chloride, 5-methoxy-3-methyl-2-[[4-[methyl(phenylmethyl)amino]phenyl]azo]thiazolium bromide, 5-methoxy-3-methyl-2-[[4-[methyl(phenylmethyl)amino]phenyl]azo]thiazolium monomethylsulfate, 5-methoxy-3-methyl-2-[[4-[methyl(phenylmethyl)amino]phenyl]azo]thiazolium acetate, 5-diethylamino-3-methyl-2-[[4-[methyl(phenylmethyl)amino]phenyl]azo]thiazolium chloride, 5-diethylamino-3-methyl-2-[[4-[methyl(phenylmethyl)amino]phenyl]azo]thiazolium bromide, 5-diethylamino-3-methyl-2-[4-[methyl(phenylmethyl)amino]phenyl]azo]thiazolium monomethylsulfate, 5-diethylamino-3-methyl-2-[[4-[methyl(phenylmethyl)amino]phenyl]azo]thiazolium acetate, 3-methyl-2-{[4-[methyl(phenylmethyl)amino]phenyl]azo}5-nitrothiazolium chloride, 3-methyl-2-{[4-[methyl(phenylmethyl)amino]phenyl]azo}5-nitrothiazolium bromide, 3-methyl-2-{[4-[methyl(phenylmethyl)amino]phenyl]azo}5-nitrothiazolium monomethylsulfate, 3-methyl-2-{[4-[methyl(phenylmethyl)amino]-2-methylphenyl]-azo}5-nitrothiazolium acetate, 2-{[4-[ethyl(phenylmethyl)amino]-2-methylphenyl]azo}-3-methylthiazolium chloride, 2-{[4-[ethyl(phenylmethyl)amino]-2-methylphenyl]azo}-3-methylthiazolium bromide, 2-{[4-[ethyl(phenylmethyl)amino]-2-methylphenyl]azo}-3-methylthiazolium monomethylsulfate, 2-{[4-[ethyl(phenylmethyl)amino]-2-methylphenyl]azo}-3-methylthiazolium acetate, 2-{[4-[ethyl(phenylmethyl)amino]-2-methylphenyl]azo}-3,4-dimethylthiazolium chloride, 2-{[4-[ethyl(phenylmethyl)amino]-2-methylphenyl]azo}-3,4-dimethylthiazolium bromide, 2-{[4-[ethyl(phenylmethyl)amino]-2-methylphenyl]azo}-3,4-dimethylthiazolium monomethylsulfate, 2-{[4-[ethyl(phenylmethyl)amino]-2-methylphenyl-azo}-3,4-dimethylthiazolium acetate, 2-{[4-[ethyl(phenylmethyl)amino]-2-methylphenyl]-azo}-3,5-dimethylthiazolium chloride, 2-{[4-[ethyl(phenylmethyl)amino]-2-methylphenyl]-azo}-3,5-dimethylthiazoliumbromide, 2-{[4-[ethyl(phenylmethyl)amino]-2-methylphenyl]-azo}-3,5-dimethylthiazolium monomethylsulfate, 2-{[4-[ethyl(phenylmethyl)amino]-2-methylphenyl]azo}-3,5-dimethylthiazolium acetate, 2-{[4-[ethyl(phenylmethyl)amino]-2-methylphenyl]azo}-3,4,5-trimethylthiazolium chloride, 2-{[4-[ethyl(phenylmethyl)amino]-2-methylphenyl]azo}-3,4,5-trimethylthiazolium bromide, 2-{[4-[ethyl(phenylmethyl)amino]-2-methylphenyl]azo}-3,4,5-trimethylthiazolium monomethylsulfate, 2-{[4-[ethyl(phenylmethyl)amino]-2-methylphenyl]azo}-3,4,5-trimethylthiazolium acetate, 5-bromo-2-{[4-[ethyl(phenylmethyl)amino]-2-methylphenyl]azo}-3-methylthiazolium chloride, 5-bromo-2-{[4-[ethyl(phenylmethyl)amino]-2-methylphenyl]azo}-3-methylthiazolium bromide, 5-bromo-2-{[4-[ethyl(phenylmethyl)amino]-2-methylphenyl]azo}-3-methylthiazolium monomethylsulfate, 5-bromo-2-{[4-[ethyl(phenylmethyl)amino]-2-methylphenyl]azo}-3-methylthiazolium acetate, 2-{[4-[ethyl(phenylmethyl)amino]-2-methylphenyl]azo}-5-methoxy-3-methylthiazolium chloride, 2-{[4-[ethyl(phenylmethyl)amino]-2-methylphenyl]azo}-5-methoxy-3-methylthiazolium bromide, 2-{[4-[ethyl(phenylmethyl)amino]-2-methylphenyl]azo}-5-methoxy-3-methylthiazolium monomethylsulfate, 2-{[4-[ethyl(phenylmethyl)amino]-2-methylphenyl]azo}-5-methoxy-3-methylthiazolium acetate, 5-diethylamino-2-{[4-[ethyl(phenylmethyl)amino]-2-methylphenyl]azo}-3-methylthiazolium chloride, 5-diethylamino-2-{[4-[ethyl(phenylmethyl)amino]-2-methylphenyl]azo}-3-methylthiazolium bromide, 5-diethylamino-2-{[4-[ethyl(phenylmethyl)amino]-2-methylphenyl]azo}-3-methylthiazolium monomethylsulfate, 5-diethylamino-2-{[4-[ethyl(phenylmethyl)amino]-2-methylphenyl-azo}-3-methylthiazolium acetate, 2-{[4-[ethyl(phenylmethyl)amino]-2-methylphenyl]azo}-3-methyl-5-nitrothiazolium chloride, 2-{[4-[ethyl(phenylmethyl)amino]-2-methylphenyl]azo}-3-methyl-5-nitrothiazolium bromide, 2-{[4-[ethyl(phenylmethyl)amino]-2-methylphenyl]azo}-3-methyl-5-nitrothiazolium monomethylsulfate, 2-{[4-[ethyl(phenylmethyl)amino]-2-methylphenyl]azo}-3-methyl-5-nitrothiazolium acetate, 3-methyl-2-{[4-[(phenylmethyl)amino]phenyl]azo}thiazolium chloride, 3-methyl-2-{[4-[(phenylmethyl)amino]phenyl]azo}thiazolium bromide, 3-methyl-2-{[4-[(phenylmethyl)amino]phenyl]azo}thiazolium monomethylsulfate, 3-methyl-2-{[4-[(phenylmethyl)amino]phenyl]azo}thiazolium acetate, 3,4-dimethyl-2-{[4-[(phenylmethyl)amino]phenyl]azo}thiazolium chloride, 3,4-dimethyl-2-{[4-[(phenylmethyl)amino]phenyl]azo}thiazolium bromide, 3,4-dimethyl-2-{[4-[(phenylmethyl)amino]phenyl]azo}thiazolium monomethylsulfate, 3,4-dimethyl-2-{[4-[(phenylmethyl)amino]phenyl]azo}thiazolium acetate, 3,5-dimethyl-2-{[4-[(phenylmethyl)amino]phenyl]azo}thiazolium chloride, 3,5-dimethyl-2-{[4-[(phenylmethyl)amino]phenyl]azo}thiazolium bromide, 3,5-dimethyl-2-{[4-[(phenylmethyl)amino]phenyl]azo}thiazolium monomethylsulfate, 3,5-dimethyl-2-{[4-[(phenylmethyl)amino]phenyl]azo}thiazolium acetate, 3,4,5-trimethyl-2-{[4-[(phenylmethyl)amino]phenyl]azo}thiazolium chloride, 3,4,5-trimethyl-2-{[4-[(phenylmethyl)amino]phenyl]azo}thiazolium bromide, 3,4,5-trimethyl-2-{[4-[(phenylmethyl)amino]phenyl]azo}thiazolium monomethylsulfate, 3,4,5-trimethyl-2-{[4-[(phenylmethyl)amino]phenyl]azo}thiazolium acetate, 5-bromo-3-methyl-2-{[4-[(phenylmethyl)amino]phenyl]azo}thiazolium chloride, 5-bromo-3-methyl-2-{[4-[(phenylmethyl)amino]phenyl]azo}thiazolium bromide, 5-bromo-3-methyl-2-{[4-[(phenylmethyl)amino]phenyl]azo}thiazolium monomethylsulfate, 5-bromo-3-methyl-2-{[4-[(phenylmethyl)amino]phenyl]azo}thiazolium acetate, 5-methoxy-3-methyl-2-{[4-[(phenylmethyl)amino]phenyl]azo}thiazolium chloride, 5-methoxy-3-methyl-2-{[4-[(phenylmethyl)amino]phenyl]azo}thiazolium bromide, 5-methoxy 3-methyl-2-{[4-[(phenylmethyl)amino]phenyl]azo}thiazolium monomethylsulfate, 5-methoxy-3-methyl-2-{[4-[(phenylmethyl)amino]phenyl]azo}thiazolium acetate, 5-diethylamino-3-methyl-2-{[4-[(phenylmethyl)amino]phenyl]azo}thiazolium chloride, 5-diethylamino-3-methyl-2-{[4-[(phenylmethyl)amino]phenyl]azo}thiazolium bromide, 5-diethylamino-3-methyl-2-{[4-[(phenylmethyl)amino]-phenyl]azo}thiazolium monomethylsulfate, 5-diethylamino-3-methyl-2-{[4-[(phenylmethyl)amino]phenyl]azo}thiazolium acetate, 3-methyl-5-nitro-2-{[4-[(phenylmethyl)amino]phenyl]azo}thiazolium chloride, 3-methyl-5-nitro-2-{[4-[(phenylmethyl)amino]phenyl]azo}thiazolium bromide, 3-methyl-5-nitro-2-{[4-[(phenylmethyl)amino]phenyl]azo}thiazolium monomethylsulfate, 3-methyl-5-nitro-2-{[4-[(phenylmethyl)amino]phenyl]

azo}thiazolium acetate, 2-{[4-bis-[(phenylmethyl)amino] phenyl]azo}-3-methyl-5-nitrothiazolium chloride, 2-{[4-bis-[(phenylmethyl)amino]phenyl]azo}-3-methyl-5-nitrothiazolium bromide, 2-{[4-bis-[(phenylmethyl)amino] phenyl]azo}-3-methyl-5-nitrothiazolium monomethylsulfate, 2-{[4-bis-[(phenylmethyl)amino]phenyl]azo}-3-methyl-5-nitrothiazolium acetate, 2-{[4-bis-[(phenylmethyl)amino]phenyl]azo}-3,4-dimethylthiazolium chloride, 2-{[4-bis-[(phenylmethyl)amino]phenyl]azo}-3,4-dimethylthiazolium bromide, 2-{[4-bis-[(phenylmethyl) amino]phenyl]azo}-3,4-dimethylthiazolium monomethylsulfate, 2-{[4-bis-[(phenylmethyl)amino]phenyl]azo}-3,4-dimethylthiazolium acetate, 2-{[4-bis[(phenylmethyl) amino]phenyl]azo}-3,5-dimethylthiazolium chloride, 2-{[4-bis[(phenylmethyl)amino]phenyl]azo}-3,5-dimethylthiazolium bromide, 2-{[4-bis[(phenylmethyl) amino]phenyl]azo}-3,5-dimethylthiazolium monomethylsulfate, 2-{[4-bis[(phenylmethyl)amino]phenyl]azo}-3,5-dimethylthiazolium acetate, 2-{[4-bis[(phenylmethyl)amino]phenyl]azo}-3,4,5-trimethylthiazolium chloride, 2-{[4-bis[(phenylmethyl)amino]phenyl]azo}-3,4,5-trimethylthiazolium bromide, 2-{[4-bis[(phenylmethyl) amino]phenyl]azo}-3,4,5-trimethylthiazolium monomethylsulfate, 2-{[4-bis[(phenylmethyl)amino]phenyl]azo}-3,4,5-trimethylthiazolium acetate, 2-{[4-bis[(phenylmethyl)amino]phenyl]azo}-5-bromo-3-methylthiazolium chloride, 2-{[4-bis[(phenylmethyl)amino]phenyl]azo}-5-bromo-3-methylthiazolium bromide, 2-{[4-bis [(phenylmethyl)amino]phenyl]azo}-5-bromo-3-methylthiazolium monomethylsulfate, 2-{[4-bis [(phenylmethyl)amino]phenyl]azo}-5-bromo-3-methylthiazolium acetate, 2-{[4-bis[(phenylmethyl)amino] phenyl]azo}-5-methoxy-3-methylthiazolium chloride, 2-{ [4-bis[(phenylmethyl)amino]phenyl]azo}-5-methoxy-3-methylthiazolium bromide, 2-{[4-bis[(phenylmethyl)amino] phenyl]azo}-5-methoxy-3-methylthiazolium monomethylsulfate, 2-{[4-bis[(phenylmethyl)amino]phenyl] azo}-5-methoxy-3-methylthiazolium acetate, 2-{[4-bis [(phenylmethyl)amino]phenyl]azo}-5-diethylamino-3-methylthiazolium chloride, 2-{[4-bis[(phenylmethyl)amino] phenyl]azo}-5-diethylamino-3-methylthiazolium bromide, 2-{[4-bis[(phenylmethyl)amino]phenyl]azo}-5-diethylamino-3-methylthiazolium monomethylsulfate, 2-{[4-bis [(phenylmethyl)amino]phenyl]azo}-5-diethylamino-3-methylthiazolium acetate, 2-{[4-bis[(phenylmethyl)amino] phenyl]azo}-3-methyl-5-nitromethylthiazolium chloride, 2-{[4-bis[(phenylmethyl)amino]phenyl]azo}-3-methyl-5-nitromethylthiazoli bromide, 2-{[4-bis[(phenylmethyl) amino]phenyl]azo}-3-methyl-5-nitromethylthiazolium monomethylsulfate and 2-{[4-bis[(phenylmethyl)amino] phenyl]azo}-3-methyl-5-nitromethylthiazolium acetate.

Particularly preferred compounds of formula (I) are: 3-methyl-2-[(4-[methyl(phenylmethyl)amino]phenyl]azo]thiazolium chloride, 3-methyl-2-[(4-[methyl(phenylmethyl) amino]phenyl]azo]thiazolium bromide, 3-methyl-2-[(4-[methyl(phenylmethyl)amino]-phenyl]azo]thiazolium monomethylsulfate, 3-methyl-2-[(4-[methyl(phenylmethyl) amino]-phenyl]azo]thiazolium acetate, 3,4-dimethyl-2-{[4-[methyl(phenylmethyl)amino]phenyl]azo}thiazolium chloride, 3,4-dimethyl-2-{[4-[methyl(phenylmethyl)amino] phenyl]azo}thiazolium bromide, 3,4-dimethyl-2-{[4-[methyl(phenylmethyl)amino]phenyl]azo}thiazolium monomethylsulfate, 3,4-dimethyl-2-{[4-[methyl(phenylmethyl)amino]phenyl]azo}thiazolium acetate, 3,5-dimethyl-2-{[4-[methyl(phenylmethyl)amino]phenyl]azo}thiazolium chloride, 3,5-dimethyl-2-{[4-[methyl(phenylmethyl)amino] phenyl]azo}thiazolium bromide, 3,5-dimethyl-2-{[4-methyl(phenylmethyl)amino]phenyl]azo}thiazolium monomethylsulfate, 3,5-dimethyl-2-{[4-[methyl(phenylmethyl) amino]phenyl]azo}thiazolium acetate, 3,4,5-trimethyl-2-{ [4-[methyl(phenylmethyl)amino]phenyl]azo}thiazolium chloride, 3,4,5-trimethyl-2-{[4-[methyl(phenylmethyl) amino]phenyl]azo}thiazolium bromide, 3,4,5-trimethyl-2-{ [4-[methyl(phenylmethyl)amino]phenyl]azo}thiazolium monomethylsulfate, 3,4,5-trimethyl-2-{[4-[methyl(phenylmethyl)amino]phenyl]azo}thiazolium acetate, 5-bromo-3-methyl-2-[(4-[methyl(phenylmethyl)amino]phenyl]azo] thiazolium chloride, 5-bromo-3-methyl-2-[(4-[methyl (phenylmethyl)amino]phenyl]azo]thiazolium bromide, 5-bromo-3-methyl-2-[(4-[methyl(phenylmethyl)amino]phenyl]azo]thiazolium monomethylsulfate, 5-bromo-3-methyl-2-[(4-[methyl(phenylmethyl)amino]phenyl]azo]thiazolium acetate, 5-methoxy-3-methyl-2-[(4-[methyl(phenylmethyl) amino]phenyl]azo]thiazolium chloride, 5-methoxy-3-methyl-2-[(4-[methyl(phenylmethyl)amino]phenyl]azo]thiazolium bromide, 5-methoxy-3-methyl-2-[(4-[methyl (phenylmethyl)amino]phenyl]azo]thiazolium monomethylsulfate, 5-methoxy-3-methyl-2-[(4-[methyl (phenylmethyl)amino]phenyl]azo]thiazolium acetate, 2-{[4-[ethyl(phenylmethyl)amino]-2-methylphenyl]azo}-3-methylthiazolium chloride, 2-{[4-[ethyl(phenylmethyl)amino]-2-methylphenyl]azo}-3-methylthiazolium bromide, 2-{[4-[ethyl(phenylmethyl)amino]-2-methylphenyl]azo}-3-methylthiazolium monomethylsulfate, 2-{[4-[ethyl (phenylmethyl)amino]-2-methylphenyl]azo}-3-methylthiazolium acetate, 2-{[4-[ethyl(phenylmethyl) amino]-2-methylphenyl]azo}-3,4-dimethylthiazolium chloride, 2-{[4-[ethyl(phenylmethyl)amino]-2-methylphenyl]azo}-3,4-dimethylthiazolium bromide, 2-{[4-[ethyl (phenylmethyl)amino]-2-methylphenyl]azo}-3,4-dimethylthiazolium monomethylsulfate, 2-{[4-[ethyl (phenylmethyl)amino]-2-methylphenyl]azo}-3,4-dimethylthiazolium acetate, 2-{[4-[ethyl(phenylmethyl) amino]-2-methylphenyl]azo}-3,5-dimethylthiazolium chloride, 2-{[4-[ethyl(phenylmethyl)amino]-2-methylphenyl]azo}-3,5-dimethylthiazolium bromide, 2-{[4-[ethyl (phenylmethyl)amino-2-methylphenyl]azo}-3,5-dimethylthiazolium monomethylsulfate, 2-{[4-[ethyl (phenylmethyl)amino]-2-methylphenyl]azo}-3,5-dimethylthiazolium acetate, 2-{[4-[ethyl(phenylmethyl) amino]-2-methylphenyl]azo}-3,4,5-trimethylthiazolium chloride, 2-{[4-[ethyl(phenylmethyl)amino]-2-methylphenyl]azo}-3,4,5-trimethylthiazolium bromide, 2-{[4-[ethyl (phenylmethyl)amino]-2-methylphenyl]azo}-3,4,5-trimethylthiazolium monomethylsulfate, 2-{[4-[ethyl (phenylmethyl)amino]-2-methylphenyl]azo}-3,4,5-trimethylthiazolium acetate, 5-bromo-2-{[4-[ethyl (phenylmethyl)amino]-2-methylphenyl]azo}-3-methylthiazolium chloride, 5-bromo-2-{[4-[ethyl (phenylmethyl)amino]-2-methylphenyl]azo}-3-methylthiazolium bromide, 5-bromo-2-{[4-[ethyl (phenylmethyl)amino]-2-methylphenyl]azo}-3-methylthiazolium monomethylsulfate, 5-bromo-2-{[4-[ethyl (phenylmethyl)amino]-2-methylphenyl]azo}-3-methylthiazolium acetate, 2-{[4-[ethyl(phenylmethyl) amino]-2-methylphenyl]azo}-5-methoxy-3-methylthiazolium chloride, 2-{[4-[ethyl(phenylmethyl) amino]-2-methylphenyl]azo}-5-methoxy-3-methylthiazolium bromide, 2-{[4-[ethyl(phenylmethyl) amino]-2-methylphenyl]azo}-5-methoxy-3-methylthiazolium monomethylsulfate and 2-{[4-[ethyl (phenylmethyl)amino]-2-methylphenyl]azo}-5-methoxy-3-methylthiazolium acetate.

The colorant of the invention contains the compounds of formula (I) in an amount from 0.01 to 10 wt. % and particularly from 0.1 to 8 wt. %.

Besides the dyes of formula (I), the colorant of the invention can additionally contain other known direct dyes from the group consisting of nitro dyes, azo dyes, anthraquinone dyes and triphenylmethane dyes as well as natural direct dyes (for example henna and indigo) alone or in admixture with one another, for example 1,4-bis[(2-hydroxyethyl)amino]-2- nitrobenzene, 1-(2-hydroxyethyl)amino-2-nitro-4-[di(2-hydroxyethyl)amino]benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino-2-nitrobenzene (HC Blue No. 11), 1-[(2,3-dihydroxypropyl)amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino-2-nitrobenzene (HC Blue No. 6), 2-[(4-amino-2-nitrophenyl)amino]-5-dimethylaminobenzoic acid (HC Blue No. 13), 1-(2-aminoethylamino)-4-[di(2-hydroxyethyl)amino]-2-nitrobenzene, 4-[d][2-hydroxyethyl)amino]-2-nitro-1-phenylamino-benzene, 1-amino-4-[(2-hydroxyethyl)amino]-2-nitrobenzene (HC Red No. 7), 2-amino-4,6-dinitrophenol, 1,4-diamino-2-nitrobenzene (C.I. 76070), 4-amino-2-nitrodiphenyl-amine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-[(2-hydroxyethyl)methylamino]-1-(methylamino)-2-nitrobenzene, 1-amino-4-[(2,3-dihydroxypropyl)amino]-5-methyl-2-nitrobenzene, 1-amino-4-(methylamino)-2-nitrobenzene, 4-amino-2-nitro-1-[(prop-2-en-1-yl)amino]benzene, 4-amino-3-nitrophenol, 4-[(2-hydroxyethyl)amino]-3-nitrophenol, 4-[(2-nitrophenyl)amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 2-amino-6-chloro-4-nitrophenl 4-[(3-hydroxypropyl)amino]-3-nitrophenol, 2,5-diamino-6-nitropyridine, 6-amino-3-[(2-hydroxyethyl)amino]-2-nitropyridine, 3-amino-6-[(2-hydroxyethyl)amino]-2-nitropypridine, 3-amino-6-(ethylamino)-2-nitropyridine, 3-[(2-hydroxyethyl)amino]-6-(methyl-amino)-2-nitropyridine, 3-amino-6-(methylamino)-2-nitropyridine, 6-(ethylamino)-3-[(2-hydroxyethyl)amino]-2-nitropyridine, 1,2,3,4-tetrahydro-6-nitroquinoxaline, 7-amino-3,4-dihydro-6-nitro-2H-1,4-benzoxazine (HC Red No. 14), 1,2-diamino-4-nitrobenzene (C.I. 76020), 1-amino-2-[(2-hydroxyethyl)amino]-5-nitrobenzene (HC Yellow No. 5), 1-(2-hydroxyethoxy)-2[(2-hydroxyethyl)amino]-5-nitrobenzene (HC Yellow No. 4), 1-[(2-hydroxyethyl)amino]-2-nitrobenzene (HC Yellow No. 2), 2-[di(2-hydroxyethyl)amino]-5-nitrophenol, 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene. 4-[(2,3-dihydroxypropyl)amino]-3-nitro-1-trifluoromethylbenzene (HC Yellow No. 6), 1-chloro-2,4-bis[(2-hydroxyethyl)amino]-5-nitrobenzene (HC Yellow No. 10), 1-amino-4-[(2-aminoethyl)amino]-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)-amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 3-[(2-hydroxyethyl)amino]-4-methyl-1-nitrobenzene, 4-chloro-3-[(2-hydroxyethyl)amino]-1-nitrobenzene, 2,4-dinitro-1-hydroxynaphthalene, 1,4-di[(2,3-dihydroxypropyl)amino]-9,10-anthraquinone, 1,4-di[(2-hydroxyethyl)amino]-9,10-anthraquinone (C.I. 61545, Disperse Blue 23), 1-[(2-hydroxyethyl)amino]-4-methylamino-9,10-anthraquinone (C.I. 61505, Disperse Blue No. 3), 2-[(2-aminoethyl)amino]-9,10-anthraquinone (HC Orange No. 5), 1-amino-4-hydroxy-9,10-anthraquinone (C.I. 60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-diketo-3,5,6,8-tetrahydroxy-2-anthracenecarboxylic acid (C.I. 75470, Natural Red 4), 1-[(3-aminopropyl)amino]-4-methyl-amino-9,10-anthraquinone (HC Blue No. 8), 1-[(3-aminopropyl)amino]-9,10-anthraquinone (HC Red No. 8), 1,4-diamino-2-methoxy-9,10-anthraquinone (C.I. 62015, Disperse Red No. 11, Solvent Violet No. 26), 1,4-dihydroxy-5, 8-bis[(2-hydroxy-ethyl)amino]-9,10-anthraquinone (C.I. 62500, Disperse Blue No. 7, Solvent Blue No. 69), 1,4-diamino-9,10-anthraquinone (C.I. 61100, Disperse Violet No. 1), 1-amino-4-(methylamino)-9,10-anthraquinone (C.I. 61105, Disperse Violet No. 4, Solvent Violet No. 12), 2-hydroxy-3-methoxy-1,4-naphthoquinone, 2,5-dihydroxy-1,4-naphthoquinone, 2-hydroxy-3-methyl-1,4-naphthoquinone, N-{6-[(3-chloro-4-(methylamino)phenyl]imino}-4-methyl-3-keto-1,4-cyclohexadien-1-yl)urea (HC Red No. 9), 2-((4-(di(2-hydroxyethyl)-amino)phenyl)amino)-5-[(2-hydroxyethyl)amino]-2,5-cyclohexadiene-1,4-dione (HC Green No. 1), 5-hydroxy-1,4-naphthoquinone (C.I. 75500, Natural Brown No. 7), 2-hydroxy-1,4-naphthoquinone (C.I. 75480, Natural Orange No. 6), 1,2-dihydro-2-(1,3-dihydro-3-keto-2H-indol-2-ylidene)-3H-3-one C.I. 73000), 1,3-bis(dicyanomethylene)indane, 9-(dimethylamino)benzo[a]phenoxazin-7-ium chloride (C.I. 51175; Basic Blue No. 6), di[4-(diethylamino)-phenyl][4-(ethylamino)naphthyl]carbenium chloride (C.I. 42595; Basic Blue No. 7), di(4-dimethylamino)phenyl)-[4-(methylphenylamino)naphthalen-1-yl]carbenium chloride (C.I. 42563; Basic Blue No. 8), 3,7-di(dimethylamino)phenothiazin-5-ium chloride (C.I. 52015; Basic Blue No. 9), di[4-(dimethylamino)phenyl][4-(phenylamino)naphthyl] carbenium chloride (C.I. 44045; Basic Blue No. 26), 2-[(4-(ethyl(2-hydroxyethyl)amino)phenyl)azo]-6-methoxy-3-methylbenzothiazolium methylsulfate (C.I. 11154; Basic Blue No. 41); Basic Blue No. 77, 8-amino-2-bromo-5-hydroxy-4-imino-6-{[3-(trimethylammonio)phenyl]amino}-1 (4H)-naphthalenone chloride (C.I. 56059; Basic Blue No. 99), bis[4-(dimethylamino)-phenyl][4-(methylamino)phenyl]carbenium chloride (C.I. 42535; Basic Violet No. 1), tris(4-amino-3-methylphenyl)carbenium chloride (C.I. 42520; Basic Violet No. 2), tris[4-(dimethylamino)phenyl]carbenium chloride (C.I. 42555; Basic Violet No. 3), 2-[3,6-(diethylamino)dibenzopyranium-9-yl]benzoyl chloride (C.I. 45170; Basic Violet No. 10), di(4-aminophenyl)(4-amino-3-methylphenyl)carbenium chloride (C.I. 42510; Basic Violet No. 14), 1,3-bis[(2,4-diamino-5-methylphenyl)azo]-3-methylbenzene (C.I. 21010; Basic Brown No. 4), 1-[(4-aminophenyl)azo]-7-(trimethylammonio)-2-naphthol chloride (C.I. 12250; Basic Brown No. 16), 3-[(4-amino-2,5-dimethoxyphenyl)azo]-N,N,N-trimethylbenzenaminium chloride (C.I. 112605; Basic Orange No. 69), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (C.I. 12251; Basic Brown No. 17) [sic], 2-[(4-aminophenyl)azo]-1,3-dimethyl-1H-imidazol-3-ium chloride (Basic Orange No. 31), 3,7-diamino-2,8-dimethyl-5-phenylphenazinium chloride (C.I. 50240; Basic Red No. 2), 1,4-dimethyl-5-{[4-(dimethylamino)phenyl]azo}-1,2,4-triazolium chloride (C.I. 11055; Basic Red No. 22), 1,3-dimethyl-2-[(4-dimethylamino)phenyl]azo-1H-imidazol-3-ium chloride (Basic Red No. 51), 2-hydroxy-1-[(2-methoxyphenyl)azo]-7-(trimethylammonio)naphthalene chloride (C.I. 12245; Basic Red No. 76), 2-{2-[(2,4-dimethoxyphenyl)amino]ethenyl}-1,3,3-trimethyl-3H-indol-1-ium chloride (C.I. 48055; Basic Yellow No. 11), 3-methyl-1-phenyl-4[(3-(trimethylammonio)phenyl] azo}pyrazol-5-one chloride (C.I. 12719; Basic Yellow No. 57), di[4-(dimethylamino)phenyl]iminomethane hydrochloride (C.I. 41000; Basic Yellow No. 2), 1-methyl-4-[(methylphenylhydrazono)methyl]pyridinium methylsulfate (Basic Yellow No. 87), bis[4-(dimethylamino)phenyl]phenylcarbenium hydrogen sulfate (1:1) (C.I. 42040; Basic Green No. 1), di[4-(dimethylamino)phenyl]phenylmethanol (C.I. 42000; Basic Green No. 4), 1-(2-morpholiniumpropylamino)-4-hydroxy-9,10-anthraquinone methylsulfate, 1-{[3-(dimethylpropylaminium)propyl]amino}-4-(methylamino)-9,10-anthraquinone chloride, 1-[(2-hydroxyethyl)amino]-3-methyl-4-[(4-nitrophenyl)azo]benzene (C.I. 11210; Disperse Red No. 17), 1-[di(2-hydroxyethyl)amino]-4-[(4-nitrophenyl)azo]benzene (Disperse Black No. 9), 4-[(4-aminophenyl) azo]-1-[di(2-hydroxyethyl)amino]-3-methylbenzene (HC Yellow No. 7), 2,6-diamino-3-[(pyridin-3-yl)azo]pyridine, 2-{[4-(acetylamino)phenyl]azo}-4-methylphenol (C.I. 11855; Disperse Yellow No. 3), 2-{[4-(ethyl-2-hydroxyethyl) amino)-2-methylphenyl]azo}-5-nitro-1,3-thiazole (C.I. 111935; Disperse Blue No. 106), 6-hydroxy-5-[(4-sulfophenyl)azo]-2-naphthalenesulfonic acid disodium salt (C.I. 15985; Food Yellow No. 3; FD&C Yellow No. 6), 2,4-dinitro-1-naphthol-7-sulfonic acid disodium salt (C.I. 10316; Acid Yellow No. 1; Food Yellow No. 1), 2-(indan-1,3-dion-2-yl) quinoline-x,x-sulfonic acid (mixture of mono- and disulfonic aid) (C.I. 47005; D&C Yellow No. 10; Food Yellow No. 13; Acid Yellow No. 3), 5-hydroxy-1-(4-sulfophenyl)-4-[(4-sulfophenyl)azo]pyrazole-3-carboxylic acid trisodium salt (C.I. 19140; Food Yellow No. 4; Acid Yellow No. 23), 9-(carboxyphenyl-6-hydroxy-3H-xanthen-3-one (C.I. 45350; Acid Yellow No. 73; D&C Yellow No. 8), 4-[(4-amino-3-sulfophenyl)azo]benzenesulfonic acid disodium salt (C.I. 13015; Acid Yellow No. 9), 5[(2,4-dinitrophenyl)amino]-2-phenylaminobenzenesulfonic acid sodium salt (C.I. 10385; Acid Orange No. 3), 4-[(2,4-dihydroxyphenyl)azo]benzenesulfonic acid monosodium salt (C.I. 14270; Acid Orange No. 6), 4-[(2-hydroxynaphth-1-yl)azo]benzenesulfonic acid sodium salt (C.I. 15510; Acid Orange No. 7), 4-[(2-hydroxynaphthalen-1-yl)azo]-3-methylbenzenesulfonic acid sodium salt (C.I. 15575; Acid Orange No. 8), 4-[(2,4-dihydroxy-3-[(2,4-dimethylphenyl)azo]phenylazo]benzenesulfonic acid sodium salt (C.I. 20170; Acid Orange No. 24), 3',6'-dihydroxy-4',5'-diiodispiro[isobenzofuran-1(3H)-9'-(9H)xanthen]-3-one (C.I. 45425; D&C Orange No. 10), 4-hydroxy-3-[(sulfonaphth-1-yl)azo]-1-naphthalenesulfonic acid disodium salt (C.I. 14720; Acid Red No. 14), 4-hydroxy-3-[(2-methoxyphenyl)azo]-1-napthalenesulfonic acid monosodium salt (C.I. 14710; Acid Red No. 4), 6-hydroxy-5-[(4-sulfonaphth-1-yl)azo]-2,4-naphthalenedisulfonic acid trisodium salt (C.I. 16255; Ponceau 4R; Acid Red No. 18), 3-hydroxy-4-[(4-sulfonaphth-1-yl)azo]-2,7-naphthalenedisulfonic acid trisodium salt (C.I. 16185; Acid Red No. 27), 8-amino-1-hydroxy-2-(phenylazo)-3,6-naphthalenedisulfonic acid disodium salt (C.I. 17200; Acid Red No. 33), 5-(acetylamino-4-hydroxy-3-[(2-methylphenyl)azo]-2,7-naphthalenedisulfonic acid disodium salt (C.I. 18065; Acid Red No. 35), 2-(3-hydroxy-2,4,5,7-tetraiododibenzopyran-6-on-9-yl)benzoic acid disodium salt (C.I. 45430; Acid Red No. 51), N-[6-(diethylamino)-9-(2,4-disulfophenyl)-3H-xanthen-3-ylidene]-N-ethylethanammonium hydroxide, inner salt, sodium salt (C.I. 45100; Acid Red No. 52), 8-{[4-(phenylazo)phenyl]azo}-7-naphthol-1,3-disulfonic acid disodium salt (C.I. 27290; Acid Red No. 73), 2',4',5',7'-tetrabromo-3',6'-dihydroxyspiro{isobenzofuran-1(3H),9'[9H]xanthen}-3-one disodium salt (C.I. 45380; Acid Red No. 87), 2',4',5',7'-tetrabromo-4,5,6,7-tetrachloro-3',6'-dihydroxyspiro{isobenzofuran-1-(3H),9'[9H]-3-one disodium salt (C.I. 45410; Acid Red No. 92), 3',6'-dihydroxy-4',5-diio-dospiro[1(3H), 9'(9H)-xanthen]-3-one disodium salt (C.I. 45425; Acid Red No. 95), 2-hydroxy-3-[(2-hydroxynaphth-1-yl)azo]-5-nitrobenzenesulfonic acid monosodium salt (C.I. 15685; Acid Red 184), (2-sulfophenyl)di[4-(ethyl ((4-sulfophenyl)-methyl)amino)phenyl]-carbenium disodium salt, betaine (C.I. 42090; Acid Blue No. 9; FD&C Blue No. 1), 3-hydroxy-4-[(4-methyl-2-sulfophenyl)azo]-2-naphthalenecarboxylic acid disodium salt (C.I. 15850; D&C Red No. 6), 6-hydroxy-5-[(2-methoxy-5-methyl-4-sulfophenyl) azo]-2-naphthalenesulfonic acid disodium salt (C.I. 16035; FD&C Red 40), 1,4-bis[(2-sulfo-4-methylphenyl)amino]-9,10-anthraquinone disodium salt (C.I. 61570; Acid Green No. 25), bis-[4-(dimethylamino)phenyl]-(3,7-disulfo-2-hydroxynaphth-1-yl)carbenium inner salt, monosodium salt (C.I. 44090; Food Green No. 4; Acid Green No. 50), bis[4-(diethylamino)phenyl](2,4-disulfophenyl)carbenium inner salt, sodium salt (2:1) (C.I. 42045; Food Blue No. 3; Acid Blue No. 1), bis[4-(diethylamino)phenyl](5-hydroxy-2,4-disulfophenyl)carbenium inner salt, calcium salt (2:1) (C.I. 42051; Acid Blue No. 3), 1-amino-4-(cyclohexylamino)-9,10 anthraquinone-2-sulfonic acid sodium salt (C.I. 62045; Acid Blue No. 62), 3,3-bis(3,5-dibromo-4-hydroxyphenyl)-4,5,6,7-tetrabromo-2,1(3H)-benzoxathiol-1,1-dioxide, 1-amino-4-(phenylamino)-9,10-anthraquinone-2-sulfonic acid (C.I. 62055; Acid Blue No. 25), 2-(1,3-dihydro-3-keto-5-sulfo-2H-indol-2-ylidene)-2,3-dihydro-3-keto-1H-in-dol 5-sulfonic acid disodium salt (C.I. 73015), Acid Blue No. 74), 9-(2-carboxyphenyl)-3-[(2-methylphenyl)amino]-6-[(2-methyl-4-sulfophenyl)amino]xanthylium inner salt, monosodium salt (C.I. 45190; Acid Violet No. 9), 1-hydroxy-4-[(4-methyl-2-sulfophenyl)amino]-9,10-anthraquinone sodium salt (C.I. 60730; D&C Violet No. 2; D&C Violet No. 43), bis{3-nitro-4-[(4-phenylamino)-3-sulfophenylamino] phenyl}sulfone (C.I. 10410; Acid Brown No. 13), 5-amino-4-hydroxy-6-[(4-nitrophenyl)azo]-3-(phenylazo)-2,7-naphthalenedisulfonic acid disodium salt (C.I. 20470; Acid Black No. 1), 3-hydroxy-4-[(2-hydroxynaphth-1-yl)azo]-7-nitro-1-naphthalenesulfonic acid chromium complex (3:2) (C.I. 15711; Acid Black No. 52), 3-[(2,4-dimethyl-5-sulfophenyl) azo]-4-hydroxy-1-naphthalenesulfonic acid disodium salt (C.I. 14700; Food Red No. 1; Ponceau SX; FD&C Red No. 4), 4-(acetylamino)-5-hydroxy-6-[(7-sulfo-4-[(4-sulfophenyl) azo]naphth-1-yl)azo]-1,7-naphthalenedisulfonic acid tetrasodium salt (C.I. 28440; Food Black No. 1) and 3-hydroxy-4-(3-methyl-5-keto-1-phenyl-4,5-dihydro-1H-pyrazol-4-ylazo)naphthalene-1-sulfonic acid sodium salt, chromium complex (Acid Red No. 195).

The colorant of the invention can contain the afore-said direct dyes in a total amount from about 0.01 to 4 wt. %, the total amount of dyes contained in the colorant of the invention being from about 0.01 to 10 wt. % and particularly from 0.1 to 8 wt. %.

Naturally, it is also possible to add to the colorant of the invention oxidation precursors (developers and couplers), for example o,p,m-phenylenediamines, o,p,m-aminophenols, diphenols or 4,5-diaminopyrazoles and suitable oxidants.

The colorant can contain each of these additional developers and couplers in a total amount from about 0.01 to 20 wt. %, preferably from about 0.1 to 10 wt. % and particularly from 0.1 to 5 wt. %.

The colorant of the invention can be in the form of, for example, a solution, particularly an aqueous or aqueous-alcoholic solution, or a cream, a gel, a surfactant-containing foaming solution (shampoo, aerosol), an emulsion or some other water-containing carrier suitable for use on hair. The colorant of the invention can also be in the form of pellets, granulate or powder which before use are dissolved in an aqueous preparation, for example water or an aqueous oxidant preparation. The composition of these agents consists of a mixture of the dye component with the additives usually employed for such preparations.

Common additives to solutions, creams, emulsions or gels are, for example, solvents such as water, the lower aliphatic monohydric or polyhydric alcohols, the esters and ethers thereof, for example alkanols, particularly those with 1 to 4 carbon atoms, for example ethanol, propanol, isopropanol, butanol, isobutanol, dihydric and trihydric alcohols, particularly those with 2 to 6 carbon atoms, for example ethylene glycol, propylene glycol, 1,3-propanediol, 1,4-butanediol, 1,5-pentanediol, 1,6-hexanediol, 1,2,6-hexanetriol, glycerol, diethylene glycol, dipropylene glycol, polyalkylene glycols such as triethylene glycol, polyethylene glycol, tripropylene glycol, polypropylene glycol, the lower alkyl ethers of polyhydric alcohols such as ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, triethylene glycol monomethyl ether and triethylene glycol monoethyl ether, ketones and ketoalcohols, particularly those with 3 to 7 carbon atoms, for example acetone, methyl ethyl ketone, diethyl ketone, methyl isobutyl ketone, methyl phenyl ketone, cyclopentanone, cyclohexanone, diacetone alcohol, ethers, for example dibutyl ether, tetrahydrofuran, dioxane, diisopropyl ether, esters, for example ethyl formate, methyl formate, methyl acetate, ethyl acetate, propyl acetate, butyl acetate, phenyl acetate, ethylene glycol monoethyl ether acetate and hydroxyethyl acetate, amides, for example dimethylformamide and dimethylacetamide, N-methylpyrrolidone as well as urea, tetramethylurea and thiodiglycol.

Moreover, the colorant of the invention can contain wetting agents or emulsifiers from the classes of anionic, cationic, amphoteric, nonionic or zwitterionic surface-active substances, for example fatty alcohol sulfates, ethoxylated fatty alcohol sulfates, alkylsulfonates, alkylbenzenesulfonates, α-olefinsulfonates, alkyltrimethylammonium salts, alkylbetaines, ethoxylated fatty alcohols, ethoxylated nonylphenols, fatty alkanolamides, ethoxylated fatty esters, fatty alcohol polyglycol ether sulfates, alkylpolyglucosides, thickeners such as the higher fatty alcohols, starch, cellulose derivatives, vaselines, paraffin oil, fatty acids and other fat constituents in emulsified form, water-soluble polymeric thickeners such as the natural gums, guar gum, xanthan gum, carob bean flour, pectin, dextran, agar, amylose, amylopectin, dextrins, clays or fully synthetic hydrocolloids, for example polyvinyl alcohol, as well as hair-care agents such as lanolin derivatives, cholesterol, pantothenic acid, water-soluble cationic polymers, protein derivatives, provitamins, vitamins, plant extracts, sugar and betaine, auxiliary agents such as moisturizers, electrolytes, antioxidants, fatty amides, sequestering agents, film-forming agents and preservatives. In addition to water, a water-soluble organic solvent or a mixture of such solvents or a water/solvent mixture can be used.

The said constituents are used in amounts normally employed for such purposes, for example the wetting agents and emulsifiers at a concentration from about 0.1 to 30 wt. %, the thickeners in an amount from about 0.1 to 30 wt. % and the hair-care agents at a concentration from about 0.1 to 5 wt. %.

The colorant of the invention has a pH from about 3 to 11 and preferably from about 3 to 10. Both organic and inorganic acids or bases are suitable for adjusting the pH according to the invention. Suitable acids are, in particular, the following: α-hydroxycarboxylic acids, for example glycolic, lactic, tartaric, citric and malic acid; ascorbic acid; gluconolactone, acetic acid, hydrochloric acid and phosphoric acid as well as mixtures of said acids. Suitable bases are, in particular, sodium carbonate, sodium hydrogen carbonate, potassium carbonate, potassium hydrogen carbonate, sodium phosphate, borax ($Na_2B_4O_7 \times 10H_2O$), disodium hydrogen phosphate, sodium hydroxide, potassium hydroxide, ammonia and other organic amines such as monoethanolamine, diethanolamine, triethanolamine, N-methyl-N-ethanolamine, N-methyl-N,N-diethanolamine, 2-(2-hydroxyethoxy)ethanolamine, di-2-(2-hydroxyethoxy)ethanamine and tri-2-(2-hydroxyethoxy)ethanamine. An alkaline pH is preferably obtained by adjustment with ammonia and/or monoethanolamine.

As a rule, the colorant of the invention is used by applying to the hair an amount of said colorant sufficient for hair dyeing namely about 30 to 120 grams depending on the length of the hair, the colorant then being allowed to act on the hair at about 15 to 50° C., preferably at 30 to 40° C., for about 1 to 60 min, preferably for 5 to 30 min, after which the hair is thoroughly rinsed with water, optionally washed with a shampoo, and then dried.

The afore-described colorant can also contain natural or synthetic polymers or modified polymers of natural origin commonly used in cosmetic agents and which fix the hair at the same time they color it. Such agents are generally referred to as tinting fixatives or dye fixatives.

Synthetic polymers that are suitable for this purpose in the cosmetic field are, for example, polyvinylpyrrolidone, polyvinyl acetate, polyvinyl alcohol and polyacrylic compounds such as polyacrylic acid and polymethacrylic acid, basic polymers of the esters of polyacrylic acid or of polymethacrylic acid and aminoalcohols, for example the salts or quaternization products thereof, polyacrylonitrile, polyvinyl acetates and the copolymers of such compounds, for example polyvinylpyrrolidone-vinyl acetate. Suitable natural polymers or modified natural polymers are, for example, chitosan (deacetylated chitin) and chitosan derivatives.

The agent of the invention can contains the afore-said polymers in an amount usually employed in such agents, particularly in an amount from about 1 to 5 wt. %. The pH of the tinting fixative or dye fixative of the invention is preferably about 4 to 10.

The hair colorant with additional fixative action is applied in the known and usual manner by moistening the hair with the fixative, arranging (setting) the hair into a hairdo and then drying.

Depending on the groups they contain, the compounds of formula (I) of the invention make it possible to achieve an outstanding, uniform, intense, brilliant and very long-lasting blue to violet coloration of keratin fibers, particularly of human hair, under gentle and skin-compatible conditions, said colorant showing excellent light stability and unusual resistance to perspiration.

The dyes in and of themselves are known. The dyes of formula (I) can be prepared by methods analogous to the known methods of preparation, for example via azo coupling of 2-aminothiazole derivatives with N-benzylaminophenyl derivatives followed by quaternization, or via oxidative condensation of thiazolone hydrazones with N-benzylaminophenyl derivatives.

The following examples will explain the subject matter of the invention in greater detail without limiting it to these examples.

EXAMPLES

Dyeing Examples 1 to 9

| | | |
|---|---|---|
| 2.5 | mmol | of dye of formula (I) |
| 5.0 | g | of ethanol |
| 4.0 | g | decylglucoside |
| 0.2 | g | ethylenediaminetetraacetic acid disodium salt |
| to 100.0 | g | water, demineralized |

When necessary, the dye solution was adjusted to the desired pH by addition of ammonia or citric acid.

The hair was dyed by applying to it an amount of colorant sufficient for hair dyeing and uniformly distributing the colorant with a brush. After a treatment time of 30 min at 40° C., the hair was rinsed with lukewarm water, washed with a shampoo, rinsed with lukewarm water and then dried.

The coloring results are summarized in the following Table 1.

Dyeing Examples 10+11

| | | |
|---|---|---|
| 2.5 | mmol | of dye of formula (I) |
| 5.0 | g | of ethanol |
| 4.0 | g | of cetyltrimethylammonium chloride (25% aqueous solution) |
| to 100.0 | g | water, demineralized |

When necessary, the dye solution was adjusted to the desired pH by addition of ammonia or citric acid.

The hair was dyed by applying to it an amount of colorant sufficient for hair dyeing and uniformly distributing the colorant with a brush. After a treatment time of 30 min at 40° C., the hair was rinsed with lukewarm water, washed with a shampoo, rinsed with lukewarm water and then dried.

The coloring results are summarized in the following Table 2.

TABLE 1

| Example | Compound of Formula (I) | pH of Colorant | Color After Dyeing | Color Values After Dyeing |
|---|---|---|---|---|
| 1 | 3-methyl-2-[[4[methyl(phenylmethyl)amino]phenyl]azo]thiazolium monomethylsulfate | 6.5 | blue | L = +16.29<br>a = +7.19<br>b = −4.51 |
| 2 | 3,4-dimethyl-2-[[4-[methyl(phenylmethyl)amino]phenyl]azo]thiazolium monomethylsulfate | 6.1 | blue | L = +18.04<br>a = +9.47<br>b = −9.58 |
| 3 | 3,5-dimethyl-2-[[4-[methyl(phenylmethyl)amino]phenyl]azo]thiazolium monomethylsulfate | 6.6 | blue | L = +18.61<br>a = +8.11<br>b = −4.25 |
| 4 | 3,4,5-trimethyl-2-[[4-[methyl(phenylmethyl)amino]phenyl]azo]thiazolium monomethylsulfate | 6.9 | blue | L = +17.90<br>a = +9.82<br>b = −11.73 |
| 5 | 5-bromo-3-methyl-2-[[4-[methyl(phenylmethyl)amino]phenyl]azo]thiazolium monomethylsulfate | 7.1 | blue | L = +18.88<br>a = +9.82<br>b = −12.83 |
| 6 | 5-methoxy-3-methyl-2-[[4-[methyl(phenylmethyl)amino]phenyl]azo]thiazolium monomethylsulfate | 7.2 | blue | L = +16.42<br>a = +6.35<br>b = −7.29 |
| 7 | 2-{[4-[ethyl(phenylmethyl)amino]-2-methtylphenyl]azo}-3-methylthiazolium monomethylsulfate | 7.5 | blue | L = +17.13<br>a = +10.09<br>b = −6.21 |
| 8 | 2-{[4-[ethyl(phenylmethyl)amino]-2-methylphenyl]azo}-3,5-dimethylthiazolium monomethylsulfate | 8.5 | blue | L = +16.84<br>a = +9.71<br>b = −7.74 |
| 9 | 2-{[4-ethyl(phenylmethyl)amino]-2-methylphenyl]azo}-5-methoxy-3-methylthiazolium monomethylsulfate | 7.7 | blue | L = +16.89<br>a = +9.70<br>b = −13.59 |

TABLE 2

| Example | Compound of Formula (I) | pH of Colorant | Color After Dyeing | Color Values After Dyeing |
|---|---|---|---|---|
| 10 | 3-methyl-2-[[4-[methyl(phenyl-methyl)amino]phenyl]azo]thiazolium monomethylsulfate | 7.0 | blue | L = +16.8<br>a = +10.9<br>b = −6.1 |
| 11 | 2-[[4-[ethyl(phenylmethyl)amino]-2-methylphenyl]azo-3-methylthia-zolium monomethyl-sulfate | 6.9 | blue | L = +18.22<br>a = +11.1<br>b = −9.6 |

Dyeing Examples 12+13

| | |
|---|---|
| 2.5 mmol | of dye of formula (I) |
| 5.0 g | of ethanol |
| 7.5 g | of coco fatty acid amidopropylbetaine (30% aqueous solution) |
| to 100.0 g | water, demineralized |

When necessary, the dye solution was adjusted to the desired pH by addition of ammonia or citric acid.

The hair was dyed by applying to it an amount of colorant sufficient for hair dyeing and uniformly distributing the colorant with a brush. After a treatment time of 30 minutes at 40° C., the hair was rinsed with lukewarm water, washed with a shampoo, rinsed with lukewarm water and then dried.

The coloring results are summarized in the following Table 3.

TABLE 3

| Example | Compound of Formula (I) | pH of Colorant | Color After Dyeing | Color Values After Dyeing |
|---|---|---|---|---|
| 12 | 3-methyl-2-[[4-[methyl(phenyl-methyl)amino]phenyl]azo]thia-zolium monomethylsulfate | 9.3 | blue | L = +17.0<br>a = +5.8<br>b = −1.6 |
| 13 | 2-[[4-[ethyl(phenylmethyl)amino]-2-methylphenyl]azo]-3-methylthiazolium monomethyl-sulfate | 9.1 | blue | L = +17.5<br>a = +8.4<br>b = −6.0 |

Dyeing Examples 14+15

| | |
|---|---|
| 2.5 mmol | of dye of formula (I) |
| 5.0 g | of ethanol |
| 7.5 g | lauryl ether sulfate (28% aqueous solution) |
| to 100.0 g | water, demineralized |

When necessary, the dye solution was adjusted to the desired pH by addition of ammonia or citric acid.

The hair was dyed by applying to it an amount of colorant sufficient for hair dyeing and uniformly distributing the colorant with a brush. After a treatment time of 30 minutes at 40° C., the hair was rinsed with lukewarm water, washed with a shampoo, rinsed with lukewarm water and then dried.

The coloring results are summarized in the following Table 4.

TABLE 4

| Example | Compound of Formula (I) | pH of Colorant | Color After Dyeing | Color Values After Dyeing |
|---|---|---|---|---|
| 14 | 3-methyl-2-[[4-[methyl(phenyl-methyl)amino]phenyl]azo]thiazolium monomethylsulfate | 9.1 | blue | L = +23.7<br>a = +29.3<br>b = −36.7 |
| 15 | 2-[[4-ethyl(phenylmethyl)amino]-2-methylphenyl]azo]-3-methyl-thiazolium monomethylsulfate | 8.9 | blue | L = +28.5<br>a = +24.3<br>b = −35.2 |

In the foregoing examples, the indicated L*a*b* color values were determined with the aid of a Chromameter II color-measuring instrument supplied by Minolta. Here the L-value stands for brightness (namely the lower the L-value, the higher is the color intensity), whereas the a-value is a measure of the red content of the color (namely the higher the a-value, the higher the red content). The b-value is a measure of the blue content of the color, namely the more negative the b-value the higher is the blue content.

Unless otherwise indicated, all percentages in the present patent application are by weight.

What Is claimed is:

1. A method for dyeing hair comprising the steps of:
   (i) applying to hair an amount of hair colorant comprising at least one thiazolium azo dye of general formula (I) sufficient for dying the hair;
   (ii) leaving the hair colorant on the hair at a temperature of 15C. to 50C. for a period of 1 to 60 minutes;
   (iii) rinsing the hair with water; and
   (iv) drying the hair;

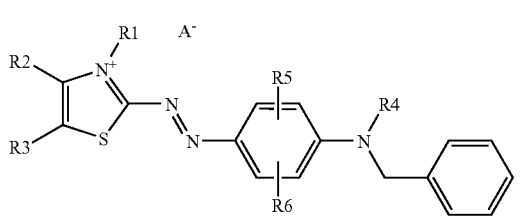

(I)

wherein:
R1 stands for a saturated or unsaturated $(C_1-C_{12})$-alkyl group, a halogen atom-substituted $(C_1-C_{12})$-alkyl group, a hydroxy-$(C_1-C_{12})$-alkyl group, a $(C_1-C_6)$-alkoxy-$(C_1-C_{12})$-alkyl group, an amino-$(C_1-C_{12})$-alkyl group, a $(C_1-C_6)$-alkylamino-$(C_1-C_{12})$-alkyl group, a di$(C_1-C_6)$-alkyl-amino-$(C_1-C_{12})$-alkyl group, a cyano-$(C_1-C_{12})$-alkyl group, a substituted or unsubstituted phenyl group or a substituted or unsubstituted benzyl group;

R2 and R3 can be equal or different and, independently of each other, stand for hydrogen, a halogen atom, a saturated or unsaturated $(C_1-C_{12})$-alkyl group, $(C_1-C_{12})$-alkoxy group, a nitro group, an amino group, a $(C_1-C_{12})$-alkylamino group, a di$(C_1-C_{12})$-alkylamino group, a $(C_1-C_{12})$-hydroxyalkylamino group, a di$(C_1-C_{12})$-hydroxyalkylamino group, a substituted or unsubstituted phenyl group or a substituted or unsubstituted heteroaryl group;

R4 stands for hydrogen, a saturated or unsaturated $(C_1-C_{12})$-alkyl group, a halogen atom-substituted $(C_1-C_{12})$-alkyl group, a hydroxy-$(C_1-C_{12})$-alkyl group, an amino-$(C_1-C_{12})$-alkyl group or a benzyl group;

R5 and R6 can be equal or different and, independently of each other, stand for hydrogen, a halogen atom, a saturated or unsaturated $(C_1-C_{12})$-alkyl group, a hydroxyl group, a $(C_1-C_{12})$-alkoxy group, a cyano group, a nitro group, an amino group, a $(C_1-C_{12})$-alkylamino group or a di$(C_1-C_{12})$-alkylamino group, and $A^-$ stands for an anion of an organic or inorganic acid.

2. The method according to claim 1, wherein R1 is a saturated or unsaturated $(C_1-C_{12})$-alkyl group.

3. The method according to claim 2, wherein R4 is a saturated or unsaturated $(C_1-C_{12})$-alkyl group.

4. The method according to claim 1, wherein $A^-$ is a chloride, bro-mide, iodide, hydrogen sulfate, sulfate, toluenesulfonate, benzenesulfonate, monomethyl-sulfate, hexafluorophosphate, hexafluoroantimonate, tetrafluoroborate, tetraphenyborate, formate, acetate or propionate anion.

5. The method according to claim 1, wherein the compound of formula (I) is selected from among 3-methyl-2-{[4-[methyl(phenylmethyl)amino]phenyl]-azo}thiazolium chloride, 3-methyl-2-{[4-[methyl(phenylmethyl)amino]phenyl]azo}thiazolium bromide, 3-methyl-2-{[4-[methyl(phenylmethyl)amino]phenyl]azo}thiazolium mono-methylsulfate, 3-methyl-2-{[4-[methyl(phenylmethyl)amino]phenyl]azo}thiazolium acetate, 3,4-dimethyl-2-{[4-[methyl(phenylmethyl)amino]phenyl]azo}thiazolium chloride, 3,4-dimethyl-2-{[4-[methyl(phenylmethyl)amino]phenyl]azo}thiazolium bromide, 3,4-dimethyl-2-{[4-[methyl(phenylmethyl)amino]phenyl]azo}thiazolium monomethylsulfate, 3,4-dimethyl-2-{[4-[methyl(phenylmethyl)amino]phenyl]azo}thiazolium acetate, 3,5-dimethyl-2-{[4-[methyl(phenylmethyl)amino]phenyl]azo}thiazolium chloride, 3,5-dimethyl-2-{[4-[methyl(phenylmethyl)amino]phenyl]azo}thiazolium bromide, 3,5-dimethyl-2-{[4-[methyl(phenylmethyl)amino]phenyl]azo}thiazolium monomethylsulfate, 3,5-dimethyl-2-{[4-[methyl(phenylmethyl)amino]phenyl]azo}thiazolium acetate, 3,4,5-trimethyl-2-{[4-[methyl(phenylmethyl)amino]phenyl]azo}thiazolium chloride, 3,4,5-trimethyl-2-{[4-[methyl(phenylmethyl)amino]phenyl]azo}thiazolium bromide, 3,4,5-trimethyl-2-{[4-[methyl(phenylmethyl)amino]phenyl]azo}thiazolium monomethylsulfate, 3,4,5-trimethyl-2-{[4-[methyl(phenylmethyl)amino]phenyl]azo}thiazolium acetate, 5-bromo-3-methyl-2-[(4-[methyl(phenylmethyl)amino]-phenyl]azo]thiazolium chloride, 5-bromo-3-methyl-2-[(4-[methyl(phenylmethyl)amino]phenyl]azo]thiazolium bromide, 5-bromo-3-methyl-2-[(4-[methyl(phenylmethyl)amino]phenyl]azo]thiazolium monomethylsulfate, 5-bromo-3-methyl-2-[(4-[methyl(phenylmethyl)amino]phenyl]azo]thiazolium acetate, 5-methoxy-3-methyl-2-[(4-[methyl(phenylmethyl)amino]phenyl]azo]thiazolium chloride, 5-methoxy-3-methyl-2-[(4-[methyl(phenylmethyl)amino]phenyl]azo]thiazolium bromide, 5-methoxy-3-methyl-2-[(4-[methyl(phenylmethyl)amino]phenyl]azo]thiazolium monomethylsulfate, 5-methoxy-3-methyl-2-[(4-[methyl (phenylmethyl)amino]phenyl]azo]thiazolium acetate, 2-{[4-[ethyl(phenylmethyl)amino]-2-methylphenyl]azo}-3-methylthiazolium chloride, 2-{[4-[ethyl(phenylmethyl)amino]-2-methylphenyl]azo}-3-methylthiazolium bromide, 2-{[4-[ethyl(phenylmethyl)amino]-2-methylphenyl]azo}-3-methylthiazolium monomethylsulfate, 2-{[4-[ethyl(phenylmethyl)amino]-2-methylphenyl]azo}-3-methylthiazolium acetate, 2-{[4-[ethyl(phenylmethyl)amino]-2-methylphenyl]azo}-3,4-dimethylthiazolium chloride, 2-{[4-[ethyl(phenylmethyl)amino]-2-methylphenyl]azo}-3,4-dimethylthiazolium bromide, 2-{[4-[ethyl(phenylmethyl)amino]-2-methylphenyl]azo}-3,4-dimethylthiazolium monomethylsulfate, 2-{[4-[ethyl(phenylmethyl)amino]-2-methylphenyl]azo}-3,4-dimethylthiazolium acetate, 2-{[4-[ethyl(phenylmethyl)amino]-2-methylphenyl]azo}-3,5-dimethylthiazolium chloride, 2-{[4-[ethyl(phenylmethyl)amino]-2-methylphenyl]azo}-3,5-dimethylthiazolium bromide, 2-{[4-[ethyl(phenylmethyl)amino]-2-methylphenyl]azo}-3,5-dimethylthiazolium monomethylsulfate, 2-{[4-[ethyl(phenylmethyl)amino]-2-methylphenyl]azo}-3,5-dimethylthiazolium acetate, 2-{[4-[ethyl(phenylmethyl)amino]-2-methylphenyl]azo}-3,4,5-trimethylthiazolium chloride, 2-{[4-[ethyl(phenylmethyl)amino]-2-methylphenyl]azo}-3,4,5-trimethylthiazolium bromide, 2-{[4-[ethyl(phenylmethyl)amino]-2-methylphenyl]azo}-3,4,5-trimethylthiazolium monomethylsulfate, 2-{[4-[ethyl(phenylmethyl)amino]-2-methylphenyl]azo}-3,4,5-trimethylthiazolium acetate, 5-bromo-2-{[4-[ethyl(phenylmethyl)amino]-2-methylphenyl]azo}-3-methylthiazolium chloride, 5-bromo-2-{[4-[ethyl(phenylmethyl)amino]-2-methylphenyl]azo}-3-methylthiazolium bromide, 5-bromo-2-{[4-[ethyl(phenylmethyl)amino]-2-methylphenyl]azo}-3-methylthiazolium monomethylsulfate, 5-bromo-2-{[4-[ethyl(phenylmethyl)amino]-2-methylphenyl]azo}-3-methylthiazolium acetate, 2-{[4-[ethyl(phenylmethyl)amino]-2-methylphenyl]azo}-5-methoxy-3-methylthiazolium chloride, 2-{[4-[ethyl(phenylmethyl)amino]-2-methylphenyl]azo}-5-methoxy-3-methylthiazolium bromide, 2-{[4-[ethyl(phenylmethyl)amino]-2-methylphenyl]azo}-5-methoxy-3-methylthiazolium monomethylsulfate and 2-{[4-[ethyl(phenylmethyl)amino]-2-methylphenyl]azo}-5-methoxy-3-methylthiazolium acetate.

6. The method according to claim 1, wherein the hair colorant contains the compound of formula (I) in an amount from 0.01 to 10 weight percent.

7. The method according to claim 1, wherein the hair is washed with a shampoo before drying.

8. A method for simultaneously dyeing and setting hair comprising the steps of:
(i) wetting the hair with an agent comprising at least one natural or synthetic polymer or modified polymer of natural origin customary for cosmetic agents and at least one thiazolium azo dye of general formula (I);
(ii) styling the hair; and
(iii) drying the hair;

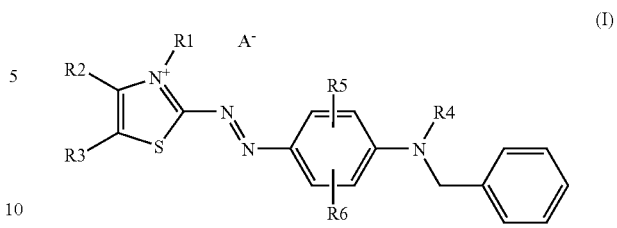

wherein:
R1 stands for a saturated or unsaturated $(C_1-C_{12})$-alkyl group, a halogen atom-substituted $(C_1-C_{12})$-alkyl group, a hydroxy-$(C_1-C_{12})$-alkyl group, a $(C_1-C_6)$-alkoxy-$(C_1-C_{12})$-alkyl group, an amino-$(C_1-C_{12})$-alkyl group, a $(C_1-C_6)$-alkylamino-$(C_1-C_{12})$-alkyl group, a di$(C_1-C_6)$-alkyl-amino-$(C_1-C_{12})$-alkyl group, a cyano-$(C_1-C_{12})$-alkyl group, a substituted or unsubstituted phenyl group or a substituted or unsubstituted benzyl group;

R2 and R3 can be equal or different and, independently of each other, stand for hydrogen, a halogen atom, a saturated or unsaturated $(C_1-C_{12})$-alkyl group, $(C_1-C_{12})$-alkoxy group, a nitro group, an amino group, a $(C_1-C_{12})$-alkylamino group, a di$(C_1-C_{12})$-alkylamino group, a $(C_1-C_{12})$-hydroxyalkylamino group, a di$(C_1-C_{12})$-hydroxyalkylamino group, a substituted or unsubstituted phenyl group or a substituted or unsubstituted heteroaryl group;

R4 stands for hydrogen, a saturated or unsaturated $(C_1-C_{12})$-alkyl group, a halogen atom-substituted $(C_1-C_{12})$-alkyl group, a hydroxy-$(C_1-C_{12})$-alkyl group, an amino-$(C_1-C_{12})$-alkyl group or a benzyl group;

R5 and R6 can be equal or different and, independently of each other, stand for hydrogen, a halogen atom, a saturated or unsaturated $(C_1-C_{12})$-alkyl group, a hydroxyl group, a $(C_1-C_{12})$-alkoxy group, a cyano group, a nitro group, an amino group, a $(C_1-C_{12})$-alkylamino group or a di$(C_1-C_{12})$-alkylamino group, and $A^-$ stands for an anion of an organic or inorganic acid.

9. The method according to claim 8 wherein R1 is a saturated or unsaturated $C_1-C_{12}$)-alkyl group.

10. The method according to claim 8 wherein R4 is a saturated or unsaturated $C_1-C_{12}$)-alkyl group.

11. The method according to claim 8 wherein $A^-$ is a chloride, bro-mide, iodide, hydrogen sulfate, sulfate, toluenesulfonate, benzenesulfonate, monomethyl-sulfate, hexafluorophosphate, hexafluoroantimonate, tetrafluoroborate, tetraphenyborate, formate, acetate or propionate anion.

12. The method according to claim 8 wherein the compound of formula (I) is selected from the group consisting of 3-methyl-2-{[4-[methyl(phenylmethyl)amino]phenyl]azo}thiazolium chloride, 3-methyl-2-{[4-[methyl(phenylmethyl)amino]phenyl]azo}thiazolium bromide, 3-methyl-2-{[4-[methyl(phenylmethyl)amino]phenyl]azo}thiazolium mono-methylsulfate, 3-methyl-2-{[4-[methyl(phenylmethyl)amino]phenyl]azo)thiazolium ace-tate, 3,4-dimethyl-2-{[4-[methyl(phenylmethyl)amino]phenyl]azo)thiazolium chloride, 3,4-dimethyl-2-{[4-[methyl(phenylmethyl)amino]phenyl]azo}thiazolium bromide, 3,4-dimethyl-2-{[4-[methyl(phenylmethyl)amino]phenyl]azo}thiazolium monomethylsulfate, 3,4-dimethyl-2-{[4-[methyl(phenylmethyl)amino]phenyl]azo}thiazolium acetate, 3,5-dimethyl-2-{[4-[methyl(phenylmethyl)amino]phenyl]azo}thiazolium chloride, 3,5-dimethyl-2-{[4-[methyl(phenylmethyl)amino]

phenyl]azo}thiazolium bromide, 3,5-dimethyl-2-{[4-[methyl(phenylmethyl)amino]phenyl]azo}thiazolium monomethylsulfate, 3,5-dimethyl-2-{[4-[methyl(phenylmethyl)amino]phenyl]azo}thiazolium acetate, 3,4,5-trimethyl-2-{[4-[methyl(phenylmethyl)amino]phenyl]azo}thiazolium chloride, 3,4,5-trimethyl-2-{[4-[methyl(phenylmethyl)amino]phenyl]azo}thiazolium bromide, 3,4,5-trimethyl-2-{[4-[methyl(phenylmethyl)amino]phenyl]azo}thiazolium monomethylsulfate, 3,4,5-trimethyl-2-{[4-[methyl(phenylmethyl)amino]phenyl]azo}thiazolium acetate, 5-bromo-3-methyl-2-[(4-[methyl(phenylmethyl)amino]phenyl]azo}thazolium chloride, 5-bromo-3-methyl-2-[(4-[methyl(phenylmethyl)amino]phenyl]azo]thiazolium bromide, 5-bromo-3-methyl-2-[(4-[methyl(phenylmethyl)amino]phenyl]azo]thiazolium monomethylsulfate, 5-bromo-3-methyl-2-[(4-[methyl(phenylmethyl)amino]phenyl]azo]thiazolium acetate, 5-methoxy-3-methyl-2-[(4-[methyl(phenylmethyl)amino]phenyl]azo]thiazolium chloride, 5-methoxy-3-methyl-2-[(4-[methyl(phenylmethyl)amino]phenyl]azo]thiazolium bromide, 5-methoxy-3-methyl-2-[(4-[methyl(phenylmethyl)amino]phenyl]azo]thiazolium monomethylsulfate, 5-methoxy-3-methyl-2-[(4-[methyl(phenylmethyl)amino]phenyl]azo]thiazolium acetate, 2-{[4-[ethyl-(phenylmethyl)amino]-2-methylphenyl]azo}-3-methylthiazolium chloride, 2-{[4-[ethyl-(phenylmethyl)amino]-2-methylphenyl]azo}-3-methylthiazolium bromide, 2-{[4-[ethyl-(phenylmethyl)amino]-2-methylphenyl]azo}-3-methylthiazolium monomethylsulfate, 2-{[4-[ethyl-(phenylmethyl)amino]-2-methylphenyl]azo}-3-methylthiazolium acetate, 2-{[4-[ethyl-(phenylmethyl)amino]-2-methylphenyl]azo}-3,4-dimethylthiazolium chloride, 2-{[4-[ethyl-(phenylmethyl)amino]-2-methylphenyl]azo}-3,4-dimethylthiazolium bromide, 2-{[4-[ethyl-(phenylmethyl)amino]-2-methylphenyl]azo}-3,4-dimethylthiazolium monomethylsulfate, 2-{[4-[ethyl-(phenylmethyl)amino]-2-methylphenyl]azo}-3,4-dimethylthiazolium acetate, 2-{[4-[ethyl-(phenylmethyl)amino]-2-methylphenyl]azo}-3,5-dimethylthiazolium chloride, 2-{[4-[ethyl-(phenylmethyl)amino]-2-methylphenyl]azo}-3,5-dimethyithiazolium bromide, 2-{[4-[ethyl-(phenylmethyl)amino]-2-methylphenyl]azo}-3,5-dimethylthiazolium monomethylsulfate, 2-{[4-[ethyl-(phenylmethyl)amino]-2-methylphenyl]azo}-3,5-dimethylthiazolium acetate, 2-{[4-[ethyl-(phenylmethyl)amino]-2-methylphenyl]azo}-3,4,5-trimethyithiazolium chloride, 2-{[4-[ethyl-(phenylmethyl)amino]-2-methylphenyl]azo}-3,4,5-trimethyithiazolium bromide, 2-{[4-[ethyl-(phenylmethyl)amino]-2-methylphenyl]azo}-3,4,5-trimethyithiazolium monomethylsulfate, 2-{[4-[ethyl-(phenylmethyl)amino]-2-methylphenyl]azo}-3,4,5-trimethylthazolium acetate, 5-bromo-2-{[4-[ethyl(phenylmethyl)amino]-2-methylphenyl]azo}-3-methylthiazolium chloride, 5-bromo-2-{[4-[ethyl(phenylmethyl)amino]-2-methylphenyl]azo}-3-methylthiazolium bromide, 5-bromo-2-{[4-[ethyl(phenylmethyl)amino]-2-methylphenyl]azo}-3-methylthiazolium monomethylsulfate, 5-bromo-2-{[4-[ethyl(phenylmethyl)amino]-2-methylphenyl]azo}-3-methylthiazolium acetate, 2-{[4-[ethyl(phenylmethyl)amino]-2-methylphenyl]azo}-5-methoxy-3-methylthiazolium chloride, 2-{[4-[ethyl(phenylmethyl)amino]-2-methylphenyl]azo}-5-methoxy-3-methylthiazolium bromide, 2-{[4-[ethyl(phenylmethyl)amino]-2-methylphenyl]azo}-5-methoxy-3-methylthiazolium monomethylsulfate and 2-{[4-[ethyl(phenylmethyl)amino]-2-methylphenyl]azo}-5-methoxy-3-methylthiazolium acetate.

13. The method according to claim 8 wherein the hair colorant contains the compound of formula (I) in an amount from 0.01 to 10 weight percent.

14. An agent for dyeing keratin fibers comprising at least one thiazolium azo dye of general formula (I) and at least one additional direct dye,

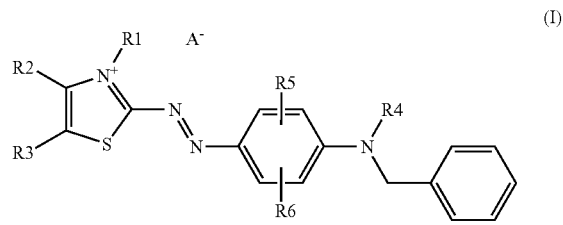

wherein:
R1 stands for a saturated or unsaturated ($C_1$-$C_{12}$)-alkyl group, a halogen atom-substituted ($C_1$-$C_{12}$)-alkyl group, a hydroxy-($C_1$-$C_{12}$)-alkyl group, a ($C_1$-$C_6$)-alkoxy-($C_1$-$C_{12}$)-alkyl group, an amino-($C_1$-$C_{12}$)-alkyl group, a ($C_1$-$C_6$)-alkylamino-($C_1$-$C_{12}$)-alkyl group, a di($C_1$-$C_6$)-alkyl-amino-($C_1$-$C_{12}$)-alkyl group, a cyano-($C_1$-$C_{12}$)-alkyl group, a substituted or unsubstituted phenyl group or a substituted or unsubstituted benzyl group;

R2 and R3 can be equal or different and, independently of each other, stand for hydrogen, a halogen atom, a saturated or unsaturated ($C_1$-$C_{12}$)-alkyl group, ($C_1$-$C_{12}$)-alkoxy group, a nitro group, an amino group, a ($C_1$-$C_{12}$)-alkylamino group, a di($C_1$-$C_{12}$)-alkylamino group, a ($C_1$-$C_{12}$)-hydroxyalkylamino group, a di($C_1$-$C_{12}$)-hydroxyalkylamino group, a substituted or unsubstituted phenyl group or a substituted or unsubstituted heteroaryl group;

R4 stands for hydrogen, a saturated or unsaturated ($C_1$-$C_{12}$)-alkyl group, a halogen atom-substituted ($C_1$-$C_{12}$)-alkyl group, a hydroxy-($C_1$-$C_{12}$)-alkyl group, an amino-($C_1$-$C_{12}$)-alkyl group or a benzyl group;

R5 and R6 can be equal or different and, independently of each other, stand for hydrogen, a halogen atom, a saturated or unsaturated ($C_1$-$C_{12}$)-alkyl group, a hydroxyl group, a ($C_1$-$C_{12}$)-alkoxy group, a cyano group, a nitro group, an amino group, a ($C_1$-$C_{12}$)-alkylamino group or a di($C_1$-$C_{12}$)-alkylamino group, and $A^-$ stands for an anion of an organic or inorganic acid.

15. The agent as defined in claim 14, wherein the agent contains the additional direct dye in a total amount from 0.01 to 4 weight percent.

16. The agent as defined in claim 14, wherein R1 is a saturated or unsaturated ($C_1$-$C_{12}$)-alkyl group.

17. The agent as defined in claim 16, wherein R4 is a saturated or unsaturated ($C_1$-$C_{12}$)-alkyl group.

18. The agent as defined in claim 14, wherein $A^-$ is a chloride, bro-mide, iodide, hydrogen sulfate, sulfate, toluenesulfonate, benzenesulfonate, monomethyl-sulfate, hexafluorophosphate, hexafluoroantimonate, tetrafluoroborate, tetraphenyborate, formate, acetate or propionate anion.

19. The agent as defined in claim 14, wherein the compound of formula (I) is selected from the group consisting of 3-methyl-2-{[4-[methyl(phenylmethyl)amino]phenyl]azo}thiazolium chloride, 3-methyl-2-{[4-[methyl(phenylmethyl)amino]phenyl]azo}thiazolium bromide, 3-methyl-2-{[4-[methyl(phenylmethyl)amino]phenyl]azo}thiazolium mono-methylsulfate, 3-methyl-2-{[4-[methyl(phenylmethyl)amino]phenyl]azo}thiazolium acetate, 3,4-dimethyl-2-{[4-[methyl(phenylmethyl)amino]phenyl]azo}thiazolium chloride, 3,4-dimethyl-2-{[4-[methyl(phenylmethyl)amino]phenyl]azo}thiazolium bromide, 3,4-dimethyl-2-{[4-[methyl(phenylmethyl)amino]phenyl]azo}thiazolium monomethylsulfate, 3,4-dimethyl-2-{[4-[methyl(phenylmethyl)amino]phenyl]azo}thiazolium acetate, 3,5-dimethyl-2-{[4-[methyl(phenylmethyl)amino]phenyl]azo}thiazolium chloride, 3,5-dimethyl-2-{[4-[methyl(phenylmethyl)amino]phenyl]azo}thiazolium bromide, 3,5-dimethyl-2-{[4-[methyl(phenylmethyl)amino]phenyl]azo}thiazolium monomethylsulfate, 3,5-dimethyl-2-{[4-[methyl(phenylmethyl)amino]phenyl]azo}thiazolium acetate, 3,4,5-trimethyl-2-{[4-[methyl(phenylmethyl)amino]phenyl]azo}thiazolium chloride, 3,4,5-trimethyl-2-{[4-[methyl(phenylmethyl)amino]phenyl]azo}thiazolium bromide, 3,4,5-trimethyl-2-{[4-[methyl(phenylmethyl)amino]phenyl]azo}thiazolium monomethylsulfate, 3,4,5-trimethyl-2-{[4-[methyl(phenylmethyl)amino]phenyl]azo}thiazolium acetate, 5-bromo-3-methyl-2-[(4-[methyl-(phenylmethyl)amino]-phenyl]azo}thiazolium chloride, 5-bromo-3-methyl-2-[(4-[methyl-(phenylmethyl)amino]phenyl]azo]thiazolium bromide, 5-bromo-3-methyl-2-[(4-[methyl-(phenylmethyl)amino]phenyl]azo]thiazolium monomethylsulfate, 5-bromo-3-methyl-2-[(4-[methyl-(phenylmethyl)amino]phenyl]azo]thiazolium acetate, 5-methoxy-3-methyl-2-[(4-[methyl(phenylmethyl)amino]phenyl]azo]thiazolium chloride, 5-methoxy-3-methyl-2-[(4-[methyl(phenylmethyl)amino]phenyl]azo]thiazolium bromide, 5-methoxy-3-methyl-2-[(4-[methyl(phenylmethyl)amino]phenyl]azo]thiazolium monomethylsulfate, 5-methoxy-3-methyl-2-[(4-[methyl(phenylmethyl)amino]phenyl]azo]thlazolium acetate, 2-{[4-[ethyl(phenylmethyl)amino]-2-methylphenyl]azo}-3-methylthiazolium chloride, 2-{[4-[ethyl(phenylmethyl)amino]-2-methylphenyl]azo}-3-methylthiazolium bromide, 2-{[4-[ethyl(phenylmethyl)amino]-2-methylphenyl]azo}-3-methylthiazolium monomethylsulfate, 2-{[4-[ethyl(phenylmethyl)amino]-2-methylphenyl]azo}-3-methylthiazolium acetate, 2-{[4-[ethyl(phenylmethyl)amino]-2-methylphenyl]azo}-3,4-dimethylthiazolium chloride, 2-{[4-[ethyl(phenylmethyl)amino]-2-methylphenyl]azo}-3,4-dimethylthiazolium bromide, 2-{[4-[ethyl(phenylmethyl)amino]-2-methylphenyl]azo}-3,4-dimethylthiazolium monomethylsulfate, 2-{[4-[ethyl(phenylmethyl)amino]-2-methylphenyl]azo}-3,4-dimethylthiazolium acetate, 2-{[4-[ethyl(phenylmethyl)amino]-2-methylphenyl]azo}-3,5-dimethyithiazolium chloride, 2-{[4-[ethyl(phenylmethyl)amino]-2-methylphenyl]azo}-3,5-dimethylthiazolium bromide, 2-{[4-[ethyl(phenylmethyl)amino]-2-methylphenyl]azo}-3,5-dimethyithiazolium monomethylsulfate, 2-{[4-[ethyl(phenylmethyl)amino]-2-methylphenyl]azo}-3,5-dimethylthiazolium acetate, 2-{[4-[ethyl(phenylmethyl)amino]-2-methylphenyl]azo}-3,4,5-trimethyithiazolium chloride, 2-{[4-[ethyl(phenylmethyl)amino]-2-methylphenyl]azo}-3,4,5-trimethyithiazolium bromide, 2-{[4-[ethyl(phenylmethyl)amino]-2-methylphenyl]azo}-3,4,5-trimethylthiazolium monomethylsulfate, 2-{[4-[ethyl(phenylmethyl)amino]-2-methylphenyl]azo}-3,4,5-trimethylthiazolium acetate, 5-bromo-2-{[4-[ethyl(phenylmethyl)amino]-2-methylphenyl]azo}-3-methylthiazolium chloride, 5-bromo-2-{[4-[ethyl(phenylmethyl)amino]-2-methylphenyl]azo}-3-methylthiazolium bromide, 5-bromo-2-{[4-[ethyl(phenylmethyl)amino]-2-methylphenyl]azo}-3-methylthiazolium monomethylsulfate, 5-bromo-2-{[4-[ethyl(phenylmethyl)amino]-2-methylphenyl]azo}-3-methylthiazolium acetate, 2-{[4-[ethyl(phenylmethyl)amino]-2-methylphenyl]azo}-5-methoxy-3-methylthiazolium cloride, 2-{[4-[ethyl(phenylmethyl)amino]-2-methylphenyi]azo}-5-methoxy-3-methylthiazolium bromide, 2-{[4-[ethyl(phenylmethyl)amino]-2-methylphenyl]azo}-5-methoxy-3-methyithiazolium monomethylsulfate and 2-{[4-[ethyl(phenylmethyl)amino]-2-methylphenyl]azo}-5-methoxy-3-methylthiazolium acetate.

20. The agent as defined in claim 14, wherein the compound of formula (I) is present in an amount from 0.01 to 10 weight percent.

21. The agent as defined in claim 14, wherein the agent has a pH from 3 to 10.

22. The agent as defined in claim 14, wherein the agent is a hair colorant.

23. An agent for dyeing keratin fibers comprising at least one thiazolium azo dye of general formula (I) and at least one natural polymer, synthetic polymer, or modified polymer of natural origin customary for cosmetic agents and is in the form of a setting tint or setting color,

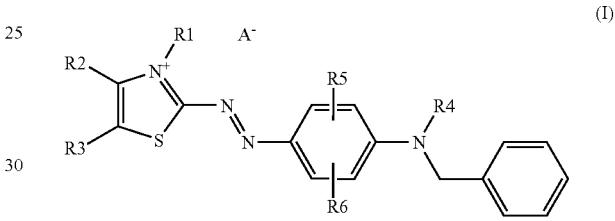

(I)

wherein:
R1 stands for a saturated or unsaturated $(C_1-C_{12})$-alkyl group, a halogen atom-substituted $(C_1-C_{12})$-alkyl group, a hydroxy-$(C_1-C_{12})$-alkyl group, a $(C_1-C_6)$-alkoxy-$(C_1-C_{12})$-alkyl group, an amino-$(C_1-C_{12})$-alkyl group, a $(C_1-C_6)$-alkylamino-$(C_1-C_{12})$-alkyl group, a di$(C_1-C_6)$-alkyl-amino-$(C_1-C_{12})$-alkyl group, a cyano-$(C_1-C_{12})$-alkyl group, a substituted or unsubstituted phenyl group or a substituted or unsubstituted benzyl group;

R2 and R3 can be equal or different and, independently of each other, stand for hydrogen, a halogen atom, a saturated or unsaturated $(C_1-C_{12})$-alkyl group, $(C_1-C_{12})$-alkoxy group, a nitro group, an amino group, a $(C_1-C_{12})$-alkylamino group, a di$(C_1-C_{12})$-alkylamino group, a $(C_1-C_{12})$-hydroxyalkylamino group, a di$(C_1-C_{12})$-hydroxyalkylamino group, a substituted or unsubstituted phenyl group or a substituted or unsubstituted heteroaryl group;

R4 stands for hydrogen, a saturated or unsaturated $(C_1-C_{12})$-alkyl group, a halogen atom-substituted $(C_1-C_{12})$-alkyl group, a hydroxy-$(C_1-C_{12})$-alkyl group, an amino-$(C_1-C_{12})$-alkyl group or a benzyl group;

R5 and R6 can be equal or different and, independently of each other, stand for hydrogen, a halogen atom, a saturated or unsaturated $(C_1-C_{12})$-alkyl group, a hydroxyl group, a $(C_1-C_{12})$-alkoxy group, a cyano group, a nitro group, an amino group, a $(C_1-C_{12})$-alkylamino group or a di$(C_1-C_{12})$-alkylamino group, and A⁻ stands for an anion of an organic or inorganic acid.

24. The agent as defined in claim 23, wherein the agent contains the additional direct dye in a total amount from 0.01 to 4 weight percent.

25. The agent as defined in claim 23, wherein R1 is a saturated or unsaturated $(C_1-C_{12})$-alkyl group.

26. The agent as defined in claim 25, wherein R4 is a saturated or unsaturated $(C_1-C_{12})$-alkyl group.

27. The agent as defined in claim 23, wherein A⁻ is a chloride, bro-mide, iodide, hydrogen sulfate, sulfate, toluenesulfonate, benzenesulfonate, monomethyl-sulfate, hexafluorophosphate, hexafluoroantimonate, tetrafluoroborate, tetraphenyborate, formate, acetate or propionate anion.

28. The agent as defined in claim 23, wherein the compound of formula (I) is selected from the group consisting of 3-methyl-2-{[4-[methyl(phenylmethyl)amino]phenyl]-azo}thiazolium chloride, 3-methyl-2-{[4-[methyl(phenylmethyl)amino]phenyl]azo}thiazolium bromide, 3-methyl-2-{[4-[methyl(phenylmethyl)amino]phenyl]azo}thiazolium mono-methylsulfate, 3-methyl-2-{[4-[methyl(phenylmethyl)amino]phenyl]azo}thiazolium ace-tate, 3,4-dimethyl-2-{[4-[methyl(phenylmethyl)amino]phenyl]azo}thiazolium chloride, 3,4-dimethyl-2-{[4-[methyl(phenylmethyl)amino]phenyl]azo}thiazolium bromide, 3,4-dimethyl-2-{[4-[methyl(phenylmethyl)amino]phenyl]azo}thiazolium monomethylsulfate, 3,4-dimethyl-2-{[4-[methyl(phenylmethyl)amino]phenyl]azo}thiazolium acetate, 3,5-dimethyl-2-{[4-[methyl(phenylmethyl)amino]phenyl]azo}thiazolium chloride, 3,5-dimethyl-2-{[4-[methyl(phenylmethyl)amino]phenyl]azo}thiazolium bromide, 3,5-dimethyl-2-{[4-[methyl(phenylmethyl)amino]phenyl]azo}thiazolium monomethylsulfate, 3,5-dimethyl-2-{[4-[methyl(phenylmethyl)amino]phenyl]azo}thiazolium acetate, 3,4,5-trimethyl-2-{[4-[methyl(phenylmethyl)amino]phenyl]azo}thiazolium chloride, 3,4,5-trimethyl-2-{[4-[methyl(phenylmethyl)amino]phenyl]azo}thiazolium bromide, 3,4,5-trimethyl-2-{[4-[methyl(phenylmethyl)amino]phenyl]azo}thiazolium monomethylsulfate, 3,4,5-trimethyl-2-{[4-[methyl(phenylmethyl)amino]phenyl]azo}thiazolium acetate, 5-bromo-3-methyl-2-[(4-[methyl(phenylmethyl)amino]phenyl]azo]thiazolium chloride, 5-bromo-3-methyl-2-[(4-[methyl(phenylmethyl)amino]phenyl]azo]thiazolium bromide, 5-bromo-3-methyl-2-[(4-[methyl(phenylmethyl)amino]phenyl]azo]thiazolium monomethylsulfate, 5-bromo-3-methyl-2-[(4-[methyl(phenylmethyl)amino]phenyl]azo]thiazolium acetate, 5-methoxy-3-methyl-2-[(4-[methyl(phenylmethyl)amino]phenyl]azo]thiazolium chloride, 5-methoxy-3-methyl-2-[(4-[methyl(phenylmethyl)amino]phenyl]azo]thiazolium bromide, 5-methoxy-3-methyl-2-[(4-[methyl(phenylmethyl)amino]phenyl]azo]thiazolium monomethylsulfate, 5-methoxy-3-methyl-2-[(4-[methyl(phenylmethyl)amino]phenyl]azo]thiazolium acetate, 2-{[4-[ethyl(phenylmethyl)amino]-2-methylphenyl]azo}-3-methylthiazolium chloride, 2-{[4-[ethyl(phenylmethyl)amino]-2-methylphenyl]azo}-3-methylthiazolium bromide, 2-{[4-[ethyl(phenylmethyl)amino]-2-methylphenyl]azo}-3-methylthiazolium monomethylsulfate, 2-{[4-[ethyl(phenylmethyl)amino]-2-methylphenyl]azo}-3-methylthiazolium acetate, 2-{[4-[ethyl(phenylmethyl)amino]-2-methylphenyl]azo}-3,4-dimethylthiazolium chloride, 2-{[4-[ethyl(phenylmethyl)amino]-2-methylphenyl]azo}-3,4-dimethylthiazolium bromide, 2-{[4-[ethyl(phenylmethyl)amino]-2-methylphenyl]azo}-3,4-dimethyithiazolium monomethylsulfate, 2-{[4-[ethyl(phenylmethyl)amino]-2-methylphenyl]azo}-3,4-dimethyithiazolium acetate, 2-{[4-[ethyl(phenylmethyl)amino]-2-methylphenyl]azo}-3,5-dimethylthiazolium chloride, 2-{[4-[ethyl(phenylmethyl)amino]-2-methylphenyl]azo}-3,5-dimethylthiazolium bromide, 2-{[4-[ethyl(phenylmethyl)amino]-2-methylphenyl]azo}-3,5-dimethylthiazolium monomethylsulfate, 2-{[4-[ethyl(phenylmethyl)amino]-2-methylphenyl]azo}-3,5-dimethylthiazolium acetate, 2-{[4-[ethyl(phenylmethyl)amino]-2-methylphenyl]azo}-3,4,5-trimethylthiazolium chloride, 2-{[4-[ethyl(phenylmethyl)amino]-2-methylphenyl]azo}-3,4,5-trimethylthiazolium bromide, 2-{[4-[ethyl(phenylmethyl)amino]-2-methylphenyl]azo}-3,4,5-trimethylthiazolium monomethylsulfate, 2-{[4-[ethyl(phenylmethyl)amino]-2-methylphenyl]azo}-3,4,5-trimethyithiazolium acetate, 5-bromo-2-{[4-[ethyl(phenylmethyl)amino]-2-methylphenyl]azo}-3-methylthiazolium chloride, 5-bromo-2-{[4-[ethyl(phenylmethyl)amino]-2-methylphenyl]azo}-3-methylthiazolium bromide, 5-bromo-2-{[4-[ethyl(phenylmethyl)amino]-2-methylphenyl]azo}-3-methylthiazolium monomethylsulfate, 5-bromo-2-{[4-[ethyl(phenylmethyl)amino]-2-methylphenyl]azo}-3-methylthiazolium acetate, 2-{[4-[ethyl(phenylmethyl)amino]-2-methylphenyl]azo}-5-methoxy-3-methylthiazolium chloride, 2-{[4-[ethyl(phenylmethyl)amino]-2-methylphenyl]azo}-5-methoxy-3-methylthiazolium bromide, 2-{[4-[ethyl(phenylmethyl)amino]-2-methylphenyl]azo}-5-methoxy-3-methylthiazolium monomethylsulfate and 2-{[4-[ethyl(phenylmethyl)amino]-2-methylphenyl]azo)-5-methoxy-3-methylthiazolium acetate.

29. The agent as defined in claim 23, wherein the compound of formula (I) is present in an amount from 0.01 to 10 weight percent.

30. The agent as defined in claim 23, wherein the agent has a pH from 3 to 10.

31. The agent as defined in claim 23, wherein the agent is a hair colorant.

32. An agent for dyeing keratin fibers comprising at least one thiazolium azo dye of general formula (I) and at least one oxidation dye precursor and wherein the agent is mixed prior to use with an oxidizing agent;

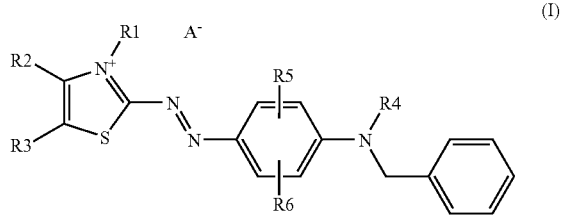

(I)

wherein:

R1 stands for a saturated or unsaturated $(C_1-C_{12})$-alkyl group, a halogen atom-substituted $(C_1-C_{12})$-alkyl group, a hydroxy-$(C_1-C_{12})$-alkyl group, a $(C_1-C_6)$-alkoxy-$(C_1-C_{12})$-alkyl group, an amino-$(C_1-C_{12})$-alkyl group, a $(C_1-C_6)$-alkylamino-$(C_1-C_{12})$-alkyl group, a di$(C_1-C_6)$-alkyl-amino-$(C_1-C_{12})$-alkyl group, a cyano-$(C_1-C_{12})$-alkyl group, a substituted or unsubstituted phenyl group or a substituted or unsubstituted benzyl group;

R2 and R3 can be equal or different and, independently of each other, stand for hydrogen, a halogen atom, a saturated or unsaturated $(C_1-C_{12})$-alkyl group, $(C_1-C_{12})$-alkoxy group, a nitro group, an amino group, a $(C_1-C_{12})$-alkylamino group, a di$(C_1-C_{12})$-alkylamino group, a $(C_1-C_{12})$-hydroxyalkylamino group, a di$(C_1-C_{12})$-hydroxyalkylamino group, a substituted or unsubstituted phenyl group or a substituted or unsubstituted heteroaryl group;

R4 stands for hydrogen, a saturated or unsaturated ($C_1$-$C_{12}$)-alkyl group, a halogen atom-substituted ($C_1$-$C_{12}$)-alkyl group, a hydroxy-($C_1$-$C_{12}$)-alkyl group, an amino-($C_1$-$C_{12}$)-alkyl group or a benzyl group;

R5 and R6 can be equal or different and, independently of each other, stand for hydrogen, a halogen atom, a saturated or unsaturated ($C_1$-$C_{12}$)-alkyl group, a hydroxyl group, a ($C_1$-$C_{12}$)-alkoxy group, a cyano group, a nitro group, an amino group, a ($C_1$-$C_{12}$)-alkylamino group or a di($C_1$-$C_{12}$)-alkylamino group, and A⁻ stands for an anion of an organic or inorganic acid.

33. The agent as defined in claim 32, wherein the agent contains the additional direct dye in a total amount from 0.01 to 4 weight percent.

34. The agent as defined in claim 32, wherein R1 is a saturated or unsaturated ($C_1$-$C_{12}$)-alkyl group.

35. The agent as defined in claim 34, wherein R4 is a saturated or unsaturated ($C_1$-$C_{12}$)-alkyl group.

36. The agent as defined in claim 32, wherein A⁻ is a chloride, bro-mide, iodide, hydrogen sulfate, sulfate, toluenesulfonate, benzenesulfonate, monomethyl-sulfate, hexafluorophosphate, hexafluoroantimonate, tetrafluoroborate, tetraphenyborate, formate, acetate or propionate anion.

37. The agent as defined in claim 32, wherein the compound of formula (I) is selected from the group consisting of 3-methyl-2-{[4-[methyl(phenylmethyl)amino]phenyl]-azo}thiazolium chloride, 3-methyl-2-{[4-[methyl(phenylmethyl)amino]phenyl]azo}thiazolium bromide, 3-methyl-2-{[4-[methyl(phenylmethyl)amino]phenyl]azo}thiazolium mono-methylsulfate, 3-methyl-2-{[4-[methyl(phenylmethyl)amino[phenyl]azo}thiazolium ace-tate, 3,4-dimethyl-2-{[4-[methyl(phenylmethyl)amino]phenyl]azo}thiazolium chloride, 3,4-dimethyl-2-{[4-[methyl(phenylmethyl)amino]phenyl]azo}thiazolium bromide, 3,4-dimethyl-2-{[4-[methyl(phenylmethyl)amino]phenyl]azo}thiazolium monomethylsulfate, 3,4-dimethyl-2-{[4-[methyl(phenylmethyl)amino]phenyl]azo}thiazolium acetate, 3,5-dimethyl-2-{[4-[methyl-(phenylmethyl)amino]phenyl]azo}thiazolium chloride, 3,5-dimethyl-2-{[4-[methyl(phenylmethyl)amino]phenyl]azo}thiazolium bromide, 3,5-dimethyl-2-{[4-[methyl(phenylmethyl)amino]phenyl]azo}thiazolium monomethylsulfate, 3,5-dimethyl-2-{[4-[methyl(phenylmethyl)amino]phenyl]azo}thiazolium acetate, 3,4,5-trimethyl-2-{[4-[methyl(phenylmethyl)amino]phenyl]azo}thiazolium chloride, 3,4,5-trimethyl-2-{[4-[methyl(phenylmethyl)amino]phenyl]azo}thiazolium bromide, 3,4,5-trimethyl-2-{[4-[methyl(phenylmethyl)amino]phenyl]azo}thiazolium monomethylsulfate, 3,4,5-trimethyl-2-{[4-[methyl(phenylmethyl)amino]phenyl]azo}thiazolium acetate, 5-bromo-3-methyl-2-[(4-[methyl-(phenylmethyl)amino]-phenyl]azo] thiazolium chloride, 5-bromo-3-methyl-2-[(4-[methyl-(phenylmethyl)amino]phenyl]azo]thiazolium bromide, 5-bromo-3-methyl-2-[(4-[methyl-(phenylmethyl)amino]phenyl]azo]thiazolium monomethylsulfate, 5-bromo-3-methyl-2-[(4-[methyl-(phenylmethyl)amino]phenyl]azo]thiazolium acetate, 5-methoxy-3-methyl-2-[(4-[methyl(phenylmethyl)amino]phenyl]azo]thiazolium chloride, 5-methoxy-3-methyl-2-[(4-[methyl(phenylmethyl)amino]phenyl]azo]thiazolium bromide, 5-methoxy-3-methyl-2-[(4-[methyl(phenylmethyl)amino]phenyl]azo]thiazolium monomethylsulfate, 5-methoxy-3-methyl-2-[(4-[methyl(phenylmethyl)amino]phenyl]azo]thiazolium acetate, 2-{[4-[ethyl(phenylmethyl)amino]-2-methylphenyl]azo}-3-methylthiazolium chloride, 2-{[4-[ethyl(phenylmethyl)amino]-2-methylphenyl]azo}-3-methylthiazolium bromide, 2-{[4-[ethyl(phenylmethyl)amino]-2-methylphenyl]azo}-3-methylthiazolium monomethylsulfate, 2-{[4-[ethyl(phenylmethyl)amino]-2-methylphenyl]azo}-3-methylthiazolium acetate, 2-{[4-[ethyl(phenylmethyl)amino]-2-methylphenyl]azo}-3,4-dimethylthiazolium chloride, 2-{[4-[ethyl(phenylmethyl)amino]-2-methylphenyl]azo}-3,4-dimethylthiazolium bromide, 2-{[4-[ethyl(phenylmethyl)amino]-2-methylphenyl]azo}-3,4-dimethylthiazolium monomethylsulfate, 2-{[4-[ethyl(phenylmethyl)amino]-2-methylphenyl]azo}-3,4-dimethylthiazolium acetate, 2-{[4-[ethyl(phenylmethyl)amino]-2-methylphenyl]azo}-3,5-dimethyithiazolium chloride, 2-{[4-[ethyl(phenylmethyl)amino]-2-methylphenyl]azo}-3,5-dimethyithiazolium bromide, 2-{[4-[ethyl(phenylmethyl)amino]-2-methylphenyl]azo}-3 5-dimethyithiazolium monomethylsulfate, 2-{[4-[ethyl(phenylmethyl)amino]-2-methylphenyl]azo}-3,5-dimethylthiazolium acetate, 2-{[4-[ethyl(phenylmethyl)amino]-2-methylphenyl]azo}-3,4,5-trimethylthiazolium chloride, 2-{[4-[ethyl(phenylmethyl)amino]-2-methylphenyl]azo}-3,4,5-trimethylthiazolium bromide, 2-{[4-[ethyl(phenylmethyl)amino]-2-methylphenyl]azo}-3,4,5-trimethylthiazolium monomethylsulfate, 2-{[4-[ethyl(phenylmethyl)amino]-2-methylphenyl]azo}-3,4,5-trimethylthiazolium acetate, 5-bromo-2-{[4-[ethyl(phenylmethyl)amino]-2-methylphenyl]azo}-3-methylthiazolium chloride, 5-bromo-2-{[4-[ethyl(phenylmethyl)amino]-2-methylphenyl]azo}-3-methylthiazolium bromide, 5-bromo-2-{[4-[ethyl(phenylmethyl)amino]-2-methylphenyl]azo}-3-methylthiazolium monomethylsulfate, 5-bromo-2-{[4-[ethyl(phenylmethyl)amino]-2-methylphenyl]azo}-3-methylthiazolium acetate, 2-{[4-[ethyl(phenylmethyl)amino]-2-methylphenyl]azo}-5-methoxy-3-methylthiazolium chloride, 2-{[4-[ethyl(phenylmethyl)amino]-2-methylphenyl]azo}-5-methoxy-3-methylthiazolium bromide, 2-{[4-[ethyl(phenylmethyl)amino]-2-methylphenyl]azo}-5-methoxy-3-methylthiazolium monomethylsulfate and 2-{[4-[ethyl(phenylmethyl)amino]-2-methylphenyl]azo}-5-methoxy-3-methylthiazolium acetate.

38. The agent as defined in claim 32, wherein the compound of formula (I) is present in an amount from 0.01 to 10 weight percent.

39. The agent as defined in claim 32, wherein the agent has a pH from 3 to 10.

40. The agent as defined in claim 32, wherein the agent is a hair colorant.

* * * * *